US012799498B2

(12) United States Patent
Zhang et al.

(10) Patent No.: US 12,799,498 B2
(45) Date of Patent: Nov. 17, 2026

(54) ***Oryza sativa* CYTOPLASMIC MALE STERILITY RESTORER GENE OSRF19 AND APPLICATION THEREOF**

(71) Applicants: HUAZHONG AGRICULTURAL UNIVERSITY, Wuhan (CN); CHINA NATIONAL SEED GROUP CORPORATION, LTD., Beijing (CN)

(72) Inventors: Qifa Zhang, Wuhan (CN); Naiyuan Wang, Beijing (CN); Fasong Zhou, Beijing (CN); Haichao Jiang, Wuhan (CN); Yidan Ouyang, Wuhan (CN); Meirong Chen, Beijing (CN)

(73) Assignees: HUAZHONG AGRICULTURAL UNIVERSITY, Wuhan (CN); CHINA NATIONAL SEED GROUP CORPORATION, LTD., Beijing (CN)

( * ) Notice: Subject to any disclaimer, the term of this patent is extended or adjusted under 35 U.S.C. 154(b) by 14 days.

(21) Appl. No.: 18/682,182

(22) PCT Filed: Jun. 22, 2022

(86) PCT No.: PCT/CN2022/100423
§ 371 (c)(1),
(2) Date: Feb. 8, 2024

(87) PCT Pub. No.: WO2023/016097
PCT Pub. Date: Feb. 16, 2023

(65) Prior Publication Data

US 2026/0015626 A1 Jan. 15, 2026

(30) Foreign Application Priority Data

Aug. 9, 2021 (CN) ......................... 202110907122.9

(51) Int. Cl.
*C12N 15/82* (2006.01)
*A01H 6/46* (2018.01)

(52) U.S. Cl.
CPC ....... *C12N 15/8289* (2013.01); *A01H 6/4636* (2018.05)

(58) Field of Classification Search
None
See application file for complete search history.

(56) References Cited

U.S. PATENT DOCUMENTS

2012/0240285 A1 9/2012 Jinushi et al.

FOREIGN PATENT DOCUMENTS

| | | | |
|---|---|---|---|
| CN | 1425770 | A | 6/2003 |
| CN | 1589325 | A | 3/2005 |
| CN | 101514342 | A | 5/2011 |
| CN | 103865937 | A | 6/2014 |
| CN | 107418956 | A | 12/2017 |
| CN | 108410882 | A | 8/2018 |
| WO | 2014/027502 | A1 | 2/2014 |

OTHER PUBLICATIONS

Xie et al (The chimeric mitochondrial gene orf182 causes non-pollentype abortion in Dongxiang cytoplasmic male-sterile rice. The Plant Journal. 95, 715-726, 2018) (Year: 2018).*

Jiang et al (Fujian cytoplasmic male sterility and the fertility restorer gene OsRf19 provide a promising breeding system for hybrid rice. PNAS. p. 1-9, 2022) (Year: 2022).*

L.I. Pingbo, et al; Genome-Wide Association Studies Reveal the Genetic Basis of Fertility Restoration of CMS-WA and CMS-HL in xian/indica and aus Accessions of Rice (*Oryza sativa* L.); Rice (NY); Jan. 29, 2020; 12 pgs.; vol. 13, No. 1.

Huiwu Tang, et al; The rice restorer Rf4 for wild-abortive cytoplasmic male sterility encodes a mitochondrial-localized PPR protein that functions in reduction of WA352 transcripts; Molecular Plant; Sep. 30, 2014; 4 Pgs.; vol. 7, No. 9.

Zhonghua Wang, et al.; Cytoplasmic male sterility of rice with boro II cytoplasm is caused by a cytotoxic peptide and is restored by two related PPR motif genes via distinct modes of mRNA silencing; Plant Cell; Mar. 31, 2006; 13 pgs.; vol. 18, No. 3. C.

China National Intellectual Property Administration; International Search Report of PCT/CN2022/100423; mailed Sep. 22, 2022; 8 pgs.

Jiang et al., “Fujian cytoplasmic male sterility and the fertility restorer gene OSRf19 provide a promising breeding system for hybrid rice,” PNAS Plant Biology, vol. 119(34), Jul. 18, 2022, pp. 1-9.

Yang, Zhengfu, “Map-Based Cloning and Functional Analysis of Male Sterility Gene TIP3 and Molecular Mechanism of Homologous Gene OSMS1 in Rice,” Ph D Dissertation, Jun. 2019, pp. 1-120.

* cited by examiner

*Primary Examiner* — Wayne Zhong
(74) *Attorney, Agent, or Firm* — Kilpatrick Townsend & Stockton LLP

(57) ABSTRACT

The present application provides an isolation, cloning, functional verification of a restorer gene OsRf19 for cytoplasmic male sterility in rice and its use in improving rice. The present application specifically provides a nucleotide sequence of the gene OsRf19 and an encoded amino acid sequence thereof, an expression vector comprising the nucleotide sequence of the gene OsRf19, a method of creating a restorer line of rice using the gene OsRf19, and a method of restoring the fertility of a cytoplasmic male sterility line of rice and producing rice hybrid seeds, and related uses.

19 Claims, 5 Drawing Sheets

Specification includes a Sequence Listing.

FIG. 4A
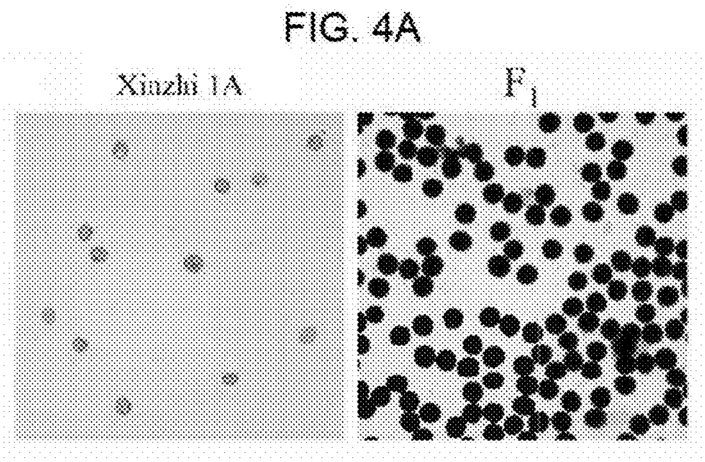
FIG. 4B

SEQUENCE LISTING

```
<160> NUMBER OF SEQ ID NOS: 9

<210> SEQ ID NO 1
<211> LENGTH: 2376
<212> TYPE: DNA
<213> ORGANISM: Oryza sativa

<400> SEQUENCE: 1

atggcgcgcc gcgccgcttc ccgcgctgtt ggcgcccttc gctcggacgg ctcgatccaa      60

gggcgaggag gccgcgcggg gggcagtggc gccgaggacg cacgccacgt gttcgacgaa     120

ttgctccgcc gtggcagggg cgcctcgatc tacggcttga accgcgccct cgccgacgtc     180

gcgcgtcaca gcccccgcggc cgccgtgtcc cgctacaacc gcatggcccg agccggcgcc    240

ggcaaggtaa ctcccaccgt gcacacctat gccatcctca tcggctgctg ctgccgcgcg     300

ggccgcttgg acctcggttt cgcggccttg ggcaatgtca ttaagaaggg atttagagtg     360

gaagccatca ccttcactcc tctgctcaag ggcctctgtg ccgacaagag gacgagcgac     420

gcaatggaca tagtgctccg cagaatgacc gagctcggct gcataccaga tgtcttctcc     480

tacaatattc ttctcaaggg tctgtgtgat gagaacagaa gccaagaagc tctcgagctg     540

ctgcacatga tggctgatga tcgaggagga ggtagcccac ctgatgttgt gtcgtatacc     600

actgtcctca atggcttctt caaagagggg gattcagaca aagcttacag tacataccat     660

gaaatgctgg accgggggat tttaccagat gttgtgacct acagctctat tattgctgcg     720

ttatgcaagg ctcaagctat ggacaaagcc atggaggtac ttaccacgat ggttaagaat     780

ggtgtcatgc ctgattgcat gacatatact agtatcatgc atggatattg ctcttcaggg     840

cagccgaaag aggctattgg atttctcaaa aagatgcgca gtgatggtgt cgaaccaaat     900

gtttttactt atagatcact gatgaattat ctttgcaaga atggaagatc caccgaagct     960

agaaagattt tcgattctat gaccaagagg ggcctagagc ctgatattgc tacctatcgt    1020

accctgcttc aggggtatgc taccaaagga gcccttgttg agatgcatgc tctcttggat    1080

ttgatggtac gaaatggtat ccaaccggat catcatgtat tcaacattct aatatgtgca    1140

tacgctaaac aagagaaagt agatcaggca atgcttgtat tcagcaaaat gaggcagcat    1200

ggattgaatc cgaatgtagt gacctatgga acagttatag atgtactttg caagtcaggc    1260

agtgtagatg atgctatgct ttattttgag cagatgatcg atgaaggact aacccctaac    1320

attattgtgt atacctccct aattcatggt ctgtgcacct atgacaagtg ggagaaggct    1380

gaagagttat tttttaaaat gttggacagt ggcatctgtc cgaacactgt tttctttagt    1440

tcaataatta gcaatctttg caaagaaggg agggttatag aatctgaaaa actttttgac    1500

ctgatggtac gtattggtgt gaagcccaat gtcattacgt acaatactct tatcgatgga    1560

tgctgcttag ctggtaagat ggatgaagca atgaagttac tttctggcat ggtctcagtt    1620
```

```
gggttgaaac ctaatactgt tacttatagc actttgatta atggctactg caaaattagt   1680
aggatggaag acgcgttagt tctttttaag gagatggaga gcagtggtgt tagtcctgat   1740
attattacgt ataacataat tctgcaaggt ttatttcaaa ccagaagaac tgctgctgca   1800
aaagaactct atgtcaggat taccgaaagt ggaatgcagc ttgaactttg gacatacaac   1860
ataatccttc atgggctttg caaaaacaat ctcactgacg aggcacttcg aatgtttcag   1920
aatctatgtt tgacggattt acagctggag actaggactt ttaacattat gattggtgcc   1980
ttacttaaat gtggaagaat ggatgaagct aaggatttgt ttgcagctct ctcggctaac   2040
ggtttagtgc cagatgttag gacctacagt ttaatggcag aaaatcttat agagcagggg   2100
ttgctagaag aattggatga tctatttctt tcaatggagg agaatggctg tactgccaac   2160
tcccgcatgc taaattccat tgttaggaaa ctgttacaga ggggtgatat aaccagggct   2220
ggcacttacc tgttcatgat tgatgagaag cacttctccc tcgaagcatc cactgcttcc   2280
ttgtttttag atcttttgtc tggggaaaaa tatcaagaat atcataggtt tctccctgaa   2340
aaatataagt cctttataga atctttgagc tgctga                             2376

<210> SEQ ID NO 2
<211> LENGTH: 2113
<212> TYPE: DNA
<213> ORGANISM: Oryza sativa

<400> SEQUENCE: 2

tcggtcccgt attttgaatc tgcggaaccg tcgctgtccc gcgtttccgt ttcgcgggat     60
gcgtatattt ttataaaacc tccccatgca tgtatataaa cataaattat tgaaaaaata    120
agtatatttg caaatttttt tcgagagctc agcactacat tgcaaagatt tgggcaactc    180
tgacaatttc catgttctac aagcttgacg tcgagggaat ggagaacctg ccaccgaata    240
gtagccctgc tatctatgtt gcgaaccatc agagtttttt ggatatctat acccttctaa    300
ctctaggaag gtgtttcaag tttataagca agacaagtat atttatgttc cgaattattt    360
gatgggcaat gtatctctta ggagtaattc ctttgcggcg tatggacagc aggagccagc    420
tggtatggct gtagtctcat ccctgctttc ttaagtagac atatatgcaa ttacagaatt    480
tggtaaacaa acaagatttt atgaatcata tatgattttg gggaaaacac caaactctct    540
ttggtggctg ccttgaacat agttctattc acacagttat agcaccttct ttaaaatgaa    600
gaactttgtt gcatacacat atggccaaac cacataatga attttgttta tttctatctt    660
tgaatgttag caccttattt tcatgcatat catgctaatt tgcttgccca cgttgagtgg    720
gaattttttt ccatgtttta taatttatat atgttctaga cttatagtcc acaatttatc    780
tacttcatgt tcctgagcct ctagtatggc tggtagcaga ctaggtgctg agtgctgtcc    840
atttttgcag actgaagaga ggagaaatac aggactgtcc gttgttagtc agatttgtaa    900
aaatagactc tgatgtagtt tattttagcc cctattttat atttaacaat acaaatatat    960
aacgtatcct aagaacttat cgtaatttag gagaagttgc tcgtttcatt aaattaaact   1020
gtgaagtaaa aatgtgtgct cgagtctgtc aatgcaatcc tgtgttcttg tttgaagata   1080
tggtgtaggg caggctagga tcgaacactg aatggtaaga ctgcttctgc cttcatttgt   1140
gcacttggtg ctgccacgcc gattaagcag tagaacaaag taattttgtc gtgcacaaat   1200
gagttatatt tcattgaaaa tcgaagtgaa aatgaaccaa aagatagaag aaaaggggaa   1260
acttggtaat tatatactcc acatgtacgc tccgtatgaa ataagttcac tttaggtcct   1320
```

ttaagttgcc tctgaattgt tcccaggccg gccgcactat tgggccaccc cataggccat 1380
gtgtacgctc cgcacagaat aatttcgctt tagctccctt aatttgtcct ctcaaacttc 1440
taaaaccagt gcaaatcttt aatttttagt tcacccattg caactcacgg gcatatttgc 1500
tagtgacata taatatgaaa cgaaggatgt agcagactat agaatttaaa ctgtgctttc 1560
attttagagc atcactaact gttatttaga tttttattta aataaatgct gaaatgatgt 1620
ttttaatcat gattaattta ataaaaatta aatccaacca tatcatatta tttcacggcg 1680
cgcggtagga aaatgcgcag ctgttgtcgc ttacggtggg agagaaggga cattgtttat 1740
ttccagaact atcttttata actcccatgg aactttaaaa taaatataat cattattata 1800
gcattagttt ttttcttgca acggacgggc atttttttc agtttccttc tgaacggaaa 1860
tttctgtttt ttttccccca ggagcgccgc gcagaagaga tcgatcgcga tctccctgcc 1920
ccgacgtcgc cggccgatct ctcattctct ccacgccctg ctcgtcgccg atctcctaca 1980
ccatccctgc catctcctcc ttcccctccc ctctatcctc cactggtgcc gcccacctct 2040
ccgtataaga caaactgcgt tgcggcgttg gtttccgccg gcgctgctgc tgcacctgtc 2100
agctagggcg ggc 2113

<210> SEQ ID NO 3
<211> LENGTH: 582
<212> TYPE: DNA
<213> ORGANISM: Oryza sativa

<400> SEQUENCE: 3
agccttttgc agctttgaaa ttctgtgttg gagttctttt ctcctacagt cgtattagag 60
gagggatctt ctctttatgt gtaaatagcg aggtatgtat gtcacctctc cgaattattt 120
ttactctggt tcctagacgg taaacaagca attatgttct gcctttgatg ccagaaaaaa 180
cacaaaagtt tgtcgttatc tctactaacg gatcataaag gaatttgtaa ctggagtttc 240
aaacttaatt tgtctaggca gtagttttgg cattagatcc aacattgtgt aggattcatt 300
tgtgtgtatc attctatagg gtttcattaa atttcgttta tgtgtactgt ttaggtgttg 360
aatagtttga cttgtttttt aactgaacaa aagatactga aatcgttcca ttcaacaaac 420
acatgttccg ttaatgaaat tattatacgt taccttttgt tttcttactc acaagtgtcc 480
tcttttctta tatcctatag attggtacaa caaattattg attcaatttt ggttttgaac 540
attgatgatc ctccctgcac tattggtgca gctgctcttc ta 582

<210> SEQ ID NO 4
<211> LENGTH: 791
<212> TYPE: PRT
<213> ORGANISM: Oryza sativa

<400> SEQUENCE: 4

Met Ala Arg Arg Ala Ala Ser Arg Ala Val Gly Ala Leu Arg Ser Asp
1 5 10 15

Gly Ser Ile Gln Gly Arg Gly Gly Arg Ala Gly Gly Ser Gly Ala Glu
20 25 30

Asp Ala Arg His Val Phe Asp Glu Leu Leu Arg Arg Gly Arg Gly Ala
35 40 45

Ser Ile Tyr Gly Leu Asn Arg Ala Leu Ala Asp Val Ala Arg His Ser
50 55 60

Pro Ala Ala Ala Val Ser Arg Tyr Asn Arg Met Ala Arg Ala Gly Ala
65 70 75 80

-continued

```
Gly Lys Val Thr Pro Thr Val His Thr Tyr Ala Ile Leu Ile Gly Cys
                85                  90                  95

Cys Cys Arg Ala Gly Arg Leu Asp Leu Gly Phe Ala Ala Leu Gly Asn
            100                 105                 110

Val Ile Lys Lys Gly Phe Arg Val Glu Ala Ile Thr Phe Thr Pro Leu
        115                 120                 125

Leu Lys Gly Leu Cys Ala Asp Lys Arg Thr Ser Asp Ala Met Asp Ile
    130                 135                 140

Val Leu Arg Arg Met Thr Glu Leu Gly Cys Ile Pro Asp Val Phe Ser
145                 150                 155                 160

Tyr Asn Ile Leu Leu Lys Gly Leu Cys Asp Glu Asn Arg Ser Gln Glu
                165                 170                 175

Ala Leu Glu Leu Leu His Met Met Ala Asp Asp Arg Gly Gly Gly Ser
            180                 185                 190

Pro Pro Asp Val Val Ser Tyr Thr Thr Val Leu Asn Gly Phe Phe Lys
        195                 200                 205

Glu Gly Asp Ser Asp Lys Ala Tyr Ser Thr Tyr His Glu Met Leu Asp
    210                 215                 220

Arg Gly Ile Leu Pro Asp Val Val Thr Tyr Ser Ser Ile Ile Ala Ala
225                 230                 235                 240

Leu Cys Lys Ala Gln Ala Met Asp Lys Ala Met Glu Val Leu Thr Thr
                245                 250                 255

Met Val Lys Asn Gly Val Met Pro Asp Cys Met Thr Tyr Thr Ser Ile
            260                 265                 270

Met His Gly Tyr Cys Ser Ser Gly Gln Pro Lys Glu Ala Ile Gly Phe
        275                 280                 285

Leu Lys Lys Met Arg Ser Asp Gly Val Glu Pro Asn Val Phe Thr Tyr
    290                 295                 300

Arg Ser Leu Met Asn Tyr Leu Cys Lys Asn Gly Arg Ser Thr Glu Ala
305                 310                 315                 320

Arg Lys Ile Phe Asp Ser Met Thr Lys Arg Gly Leu Glu Pro Asp Ile
                325                 330                 335

Ala Thr Tyr Arg Thr Leu Leu Gln Gly Tyr Ala Thr Lys Gly Ala Leu
            340                 345                 350

Val Glu Met His Ala Leu Leu Asp Leu Met Val Arg Asn Gly Ile Gln
        355                 360                 365

Pro Asp His His Val Phe Asn Ile Leu Ile Cys Ala Tyr Ala Lys Gln
    370                 375                 380

Glu Lys Val Asp Gln Ala Met Leu Val Phe Ser Lys Met Arg Gln His
385                 390                 395                 400

Gly Leu Asn Pro Asn Val Val Thr Tyr Gly Thr Val Ile Asp Val Leu
                405                 410                 415

Cys Lys Ser Gly Ser Val Asp Asp Ala Met Leu Tyr Phe Glu Gln Met
            420                 425                 430

Ile Asp Glu Gly Leu Thr Pro Asn Ile Ile Val Tyr Thr Ser Leu Ile
        435                 440                 445

His Gly Leu Cys Thr Tyr Asp Lys Trp Glu Lys Ala Glu Glu Leu Phe
    450                 455                 460

Phe Lys Met Leu Asp Ser Gly Ile Cys Pro Asn Thr Val Phe Phe Ser
465                 470                 475                 480

Ser Ile Ile Ser Asn Leu Cys Lys Glu Gly Arg Val Ile Glu Ser Glu
                485                 490                 495

Lys Leu Phe Asp Leu Met Val Arg Ile Gly Val Lys Pro Asn Val Ile
```

```
            500                 505                 510

Thr Tyr Asn Thr Leu Ile Asp Gly Cys Cys Leu Ala Gly Lys Met Asp
        515                 520                 525

Glu Ala Met Lys Leu Leu Ser Gly Met Val Ser Val Gly Leu Lys Pro
    530                 535                 540

Asn Thr Val Thr Tyr Ser Thr Leu Ile Asn Gly Tyr Cys Lys Ile Ser
545                 550                 555                 560

Arg Met Glu Asp Ala Leu Val Leu Phe Lys Glu Met Glu Ser Ser Gly
                565                 570                 575

Val Ser Pro Asp Ile Ile Thr Tyr Asn Ile Ile Leu Gln Gly Leu Phe
            580                 585                 590

Gln Thr Arg Arg Thr Ala Ala Ala Lys Glu Leu Tyr Val Arg Ile Thr
        595                 600                 605

Glu Ser Gly Met Gln Leu Glu Leu Trp Thr Tyr Asn Ile Ile Leu His
    610                 615                 620

Gly Leu Cys Lys Asn Asn Leu Thr Asp Glu Ala Leu Arg Met Phe Gln
625                 630                 635                 640

Asn Leu Cys Leu Thr Asp Leu Gln Leu Glu Thr Arg Thr Phe Asn Ile
                645                 650                 655

Met Ile Gly Ala Leu Leu Lys Cys Gly Arg Met Asp Glu Ala Lys Asp
            660                 665                 670

Leu Phe Ala Ala Leu Ser Ala Asn Gly Leu Val Pro Asp Val Arg Thr
        675                 680                 685

Tyr Ser Leu Met Ala Glu Asn Leu Ile Glu Gln Gly Leu Leu Glu Glu
    690                 695                 700

Leu Asp Asp Leu Phe Leu Ser Met Glu Glu Asn Gly Cys Thr Ala Asn
705                 710                 715                 720

Ser Arg Met Leu Asn Ser Ile Val Arg Lys Leu Leu Gln Arg Gly Asp
                725                 730                 735

Ile Thr Arg Ala Gly Thr Tyr Leu Phe Met Ile Asp Glu Lys His Phe
            740                 745                 750

Ser Leu Glu Ala Ser Thr Ala Ser Leu Phe Leu Asp Leu Leu Ser Gly
        755                 760                 765

Gly Lys Tyr Gln Glu Tyr His Arg Phe Leu Pro Glu Lys Tyr Lys Ser
    770                 775                 780

Phe Ile Glu Ser Leu Ser Cys
785                 790


<210> SEQ ID NO 5
<211> LENGTH: 41
<212> TYPE: DNA
<213> ORGANISM: Artificial Sequence
<220> FEATURE:
<223> OTHER INFORMATION: Synthesized primer sequence with the cutting
      site of restriction endonuclease BamHI

<400> SEQUENCE: 5

gagctcggta cccggggatc ctcggtcccg tattttgaat c                         41


<210> SEQ ID NO 6
<211> LENGTH: 41
<212> TYPE: DNA
<213> ORGANISM: Artificial Sequence
<220> FEATURE:
<223> OTHER INFORMATION: Synthesized primer sequence with the cutting
      site of restriction endonuclease PstI

<400> SEQUENCE: 6
```

-continued

```
gccaagcttg catgcctgca gtagaagagc agctgcacca a                         41


<210> SEQ ID NO 7
<211> LENGTH: 20
<212> TYPE: DNA
<213> ORGANISM: Artificial Sequence
<220> FEATURE:
<223> OTHER INFORMATION: Synthesized primer sequence used for RT-PCR in
      expression analysis of OsRf18

<400> SEQUENCE: 7

gatgtacttt gcaagtcagg                                                 20


<210> SEQ ID NO 8
<211> LENGTH: 20
<212> TYPE: DNA
<213> ORGANISM: Artificial Sequence
<220> FEATURE:
<223> OTHER INFORMATION: Synthesized primer sequence used for RT-PCR in
      expression analysis of OsRf18

<400> SEQUENCE: 8

ccttctttgc aaagattgct                                                 20


<210> SEQ ID NO 9
<211> LENGTH: 549
<212> TYPE: DNA
<213> ORGANISM: Oryza sativa

<400> SEQUENCE: 9

atgatgagat ttagttcaac ggataagaag gatagaagaa atatgctatt tgctgctatt     60

ccatctattt ggaaattcat ggacaacatt ttttttggtg gacctgggat gactatgcat    120

agcttaccac ttttcgtagt aaagaggctt gccgacactt gcgtgccagg cggcgctttc    180

ctgattgcac ttttgtgcag tctctcttcc acggcaatgg ccgctggtcc atccgactgg    240

atgcggggtg atccaaatga aacactccta cggcagaccg ataagcaaat agagaaggtc    300

aacgaggagt taaggaacgt gacatcccaa gccgtggaaa aagcgcagca gttccagttg    360

aacttgccgg gcacaagtga ggaacaaacg cacaccatcc gttctattct agaacatgat    420

cttgatggta tcgctctgaa tcaacgactt cgacgaatcc gaagatgggt caattctgga    480

gaaatcgaga atccggaaag cctattttgg cttcaaatta ttgaccaatt cagcaagtgg    540

ttcccatga                                                            549
```

*Oryza sativa* CYTOPLASMIC MALE STERILITY RESTORER GENE OSRF19 AND APPLICATION THEREOF

CROSS-REFERENCE TO RELATED APPLICATIONS

This application is a § 371 National Stage application of PCT/CN2022/100423, filed on Jun. 22, 2022, which claims the priority under Article 8 of the PCT to Chinese Patent Application No. 202110907122.9, filed on Aug. 9, 2021, the entire contents of each of which are incorporated herein by reference.

SEQUENCE LISTING

A Sequence Listing conforming to the rules of WIPO Standard ST.25 is hereby incorporated by reference. Said Sequence Listing has been filed as an electronic document via ASCII text. The electronic document, created on Aug. 29, 2025, is entitled "23C83242US-Revised ST25 Sequence Listing-2025-8-29" and is 15,817 bytes in size.

TECHNICAL FIELD

The present application relates to the field of plant genetic engineering, and more particularly, to the cloning, isolation, and functional verification of a restorer gene OsRf19 for controlling cytoplasmic male sterility in rice and its use in rice improvement.

BACKGROUND

During plant development, a biological phenomenon, in which the degeneration of the male reproductive system due to environmental conditions or self-genetic mutations results in the inability to produce pollens or lack of normal function of the pollens produced, but the female reproductive system is normally developed, is called as male sterility. Crop varieties or lines with male sterility genetic characteristics are referred to as sterility lines. While some crop varieties (lines), which are referred to as restorer lines, can restore normal fertility to hybrids produced by crossing with sterility lines. Sterility lines and restorer lines have important application value in utilization of crop heterosis and cross breeding.

Currently, studies on male sterility and its fertility restoration have been reported in a variety of crops such as wheat, corn, rape and rice (*Oryza sativa*), and have been used on a large scale in the production of hybrid species. Male sterility includes nuclear sterility controlled by nuclear genes and cytoplasmic male sterility (CMS) controlled by cytoplasmic genes. The nuclear male sterility genes in rice are mainly pms3 and tms5, etc., and their fertility is affected by light and temperature. On this basis, a two-line rice breeding method was proposed. The two-line breeding method flexibly utilizes the fertility transformation characteristic of the nuclear sterility line, and has many advantages such as simple genetic behavior of sterility, wide restoration sources and the like. However, the fertility of the two-line nuclear sterility line is easily affected by the fluctuation of light and temperature conditions, which causes many difficulties for the reproduction of the sterility line and the seed production of the hybrids. The three-line hybrid breeding is genetically based on cytoplasmic male sterility line and its maintainer and restorer lines. Proteins encoded by specific genes in the mitochondrial genome of a sterility line can lead to male sterility. The maintainer line has a normal cytoplasm with the same nuclear genome as the sterility line, and its pollens are normally fertile and have self-fruitfulness. Crossing of a maintainer line with the sterility line can produce seeds of the sterility line, allowing the sterility line to reproduce. The nuclear genome of the restorer line carries a gene having a restoring function whose pollens are normally fertile and have self-fruitfulness. The restorer line is crossed with the sterility line to produce seeds of the hybrid F1, which have formal fertility. Three-line hybrid breeding makes full use of heterosis and ensures the safety of grain production.

The main types of cytoplasmic male sterility in rice include "Yebai", "Baotai", "Honglian", and so on. Domestic hybrid rice mainly takes advantage of the type "Yebai". "Yebai" sterility line (CMS-WA) is a cytoplasmic male sterility line of indica type rice, which is the earliest type used in three-line hybrid rice in China. CMS-WA possesses the most hybrid combinations, and is the mainest type in the production up to now. In recent years, the cultured combinations and cultivated areas of the cytoplasmic sterility type, such as "water-printing type", "Gang type", "D type" and "Aibai type", which show an ascending trend, also have a similar restoration and maintenance relationship with the sterility lines of "Yebai" type. The sterility lines of "Yebai" type involve sporophytic sterility, and it is believed that cytoplasmic male sterility and restoration of the "Yebai" type are not only affected by two pairs of major genes, and may also be modified by minor genes. Most studies have reported that the inheritance of the male sterility restorer gene of the "Yebai" type is controlled by two pairs of genes, which are independently inherited and have a certain interaction effect. Yao (1997) et al.'s genetic studies on fertility restoration using Zhenshan 97A and Minghui 63 of the "Yebai" type concluded that the restorer line Minghui 63 of the "Yebai" type had two pairs of dominant restorer genes. Subsequently, Rf4 was localized and cloned using the genetic populations constructed by IR24 and Minghui 63, respectively, and it was found by sequence analysis that it encodes a protein of the PPR (pentatricopeptide repeat proteins) structure (Tang et al. 2014; Kazama et al. 2014).

The cytoplasmic male sterility of rice Honglian type (CMS-HL) is derived from the wild rice Hongmang and is of the indica-type cytoplasmic male sterility line type. However, Honglian and Yebai types are obviously different in the terms of restoration and maintenance relationship, genetic characteristics and cytological characteristics of pollen abortion, and the former belongs to a typical gametophyte sterility type. For the mapping of the restorer gene of the Honglian type, Huang Qingyang et al. (1999) mapped the male sterility restorer gene Rf-5 of the Honglian type to chromosome 10 by SSR markers at a genetic distance of 7.8 cM from RM258. Huang et al. (2012) constructed $F_2$ and $BC_1F_1$ populations by Yuetai A and 9311 to map the two restorer genes Rf5 and Rf6 of the cytoplasmic male sterility rice of the Honglian type to between the markers RM6469 and RM25661 on chromosome 10, and between the markers RM3710 and RM22242 on chromosome 8, respectively. It was also found that 50% of the pollens in the $F_1$ plants carrying only one restorer gene of Rf5 or Rf6 were fertile, while 75% of the pollens in the hybrids carrying both Rf5 and Rf6 were normally fertile. $F_1$ plants carrying two non-allelic restorer genes have higher seed setting rates under stress conditions than $F_1$ plants carrying only one restorer gene (Huang et al., 2012). Hu et al., in 2012, cloned the restorer gene Rf5 of cytoplasmic male sterility of the Honglian type (Hu et al., 2012), and Huang et al., in 2015, cloned another restorer gene Rf6 of cytoplasmic male sterility of the Honglian type (Huang et al., 2015), and studied their regulatory mechanisms.

Presently widely used japonica sterility lines are mainly cytoplasmic male sterility of the Baotai type (CMS-BT), belonging to a gametophyte sterility type. Japanese scholar Shinjyo (1975) studied in detail the selection and inheritance of the three lines of the Baotai type and concluded that the restoration of the male sterility line of the Baotai type was controlled by a pair of dominant genes. In 1996, Akagi et al., using two near-isogenic lines as materials, detected a co-dominant marker OSRRf linked to the restorer gene Rf-1 by an ISSR molecular marker, and this marker was located on chromosome 10 at a genetic distance of 3.7±1.1 cM from Rf-1. Komori et al. (2003) selected nine RFLP markers known to be linked to Rf-1 on chromosome 10 and used an isolated population of 1024 individuals for fine mapping of the restorer gene of the Baotou-type, resulting in fine mapping of Rf-1 within the S12564Tsp5091 and C1361MwoI regions. Subsequently, Komori et al. cloned the restorer gene Rf-1 of the cytoplasmic male sterility line of the Baotou-type by map-based cloning (Komori et al., 2004). The Liu Yaoguang group in South China Agricultural University discoveried in 2006 that the restorer gene, Rf-1, of the cytoplasmic male sterility line of the Baotou-type comprised two restorer genes, Rfla and Rflb, and studied the mechanism of cytoplasmic male sterility and fertility restoration function of rice CMS-BT were studied (Wang et al., 2006).

Although great progress has been made in the breeding of hybrid rice in China, there have been some problems to be solved for a long time. One of the main reasons is that the sterile cytoplasm used in the present production is mainly the cytoplasm of the Yebai type, and the fertility restoration of the hybrid rice requires that co-existence of the Rf3 and Rf4 genes to meet the requirements of the production, which leads to the difficulties in breeding of new restorer lines. On the other hand, the fertility of the cytoplasmic male sterility line of the Yebai type is not stable enough to self-cross to produce seeds in high-temperature weather, and false hybrids occur in seed production, resulting in a lack of seed purity (Xi Jianmin et al., 2011; GE Xiaoping, 2012). Many excellent rice germplasm resources cannot be utilized as parents of the maintainer lines of the Yebai type, resulting in narrow genetic bases between parents, and greatly limiting the potential for yield improvement. Wang Naiyuan et al., in studying the genetic expression of rice male sterility in heterologous cytoplasmic background, found a new type of male sterility cytoplasm, named CMS-FA type cytoplasm, from common wild-type rice, and bred a series of new cytoplasm source sterility lines, which widened the breeding path of high-quality rice hybrid rice (Wang Naiyuan, 2006a). On the basis of this study, a new male sterility restorer line was developed, and the three-line matching and utilization of a new seed source was achieved (Wang Naiyuan, 2006b). The sterility line cultilated from new male sterile cytoplasmic source has a wide range of maintainer line sources, which can not only extend the maintainer line sources to various fields such as medium rice, late rice, and high-quality rice, but also break the genetic limitation of the early indica rice system in the Yangtze River, thus greatly improving the breeding potential of the sterility line (Wang Naiyuan et al., 2008a). Unlike maintainer lines, new male sterility restorer lines in conventional varieties have limited resources, and current studies have shown that the restorer gene is controlled by a pair of dominant genes (Wang Naiyuan et al., 2008b). Based on this consideration, by cloning a restorer gene capable of restoring a new male sterility line (CMS-FA) and combining a molecular breeding tool, the restorer gene can be quickly and effectively transferred to a good breeding resource, thereby greatly widening the source of the restorer line and making full use of the heterosis, which is beneficial to ensuring food security in China.

SUMMARY

The object of the present application is to isolate and clone a restorer gene OsRf19 capable of restoring the fertility of cytoplasmic male sterility from rice. The object of the present application is to improve the restoring ability of rice in terms of crossing and mating with a sterility line by studying and applying the restorer gene OsRf19 of the fertility, and to provide a new gene resource for rice genetic breeding.

The present application makes use of a map-based cloning method to isolate and clone a gene OsRf19 which controls the fertility restoration of cytoplasmic male sterility of a new type of rice, thereby providing a new gene resource for three-line mating breeding of rice. In particular, the present application relates to the following technical solutions.

In a first aspect, the present application provides a restorer gene OsRf19 for cytoplasmic male sterility in rice comprising the nucleotide sequence set forth in SEQ ID NO: 1.

In a second aspect, the present application provides a protein encoded by a restorer gene OsRf19 for cytoplasmic male sterility in rice comprising or consisting of the amino acid sequence set forth in SEQ ID NO: 4.

In a third aspect, the application provides a nucleic acid encoding the protein of the second aspect.

In a fourth aspect, the present application provides an expression vector comprising the restorer gene OsRf19 for cytoplasmic male sterility in rice of the first aspect or the nucleic acid of the third aspect.

In a fifth aspect, the present application provides a method of creating a restorer line of rice, which comprises introducing into a rice variety the restorer gene OsRf19 for cytoplasmic male sterility in rice of the first aspect or the nucleic acid of the third aspect or the expression vector of the fourth aspect.

In a sixth aspect, the present application provides a method of restoring the fertility of a cytoplasmic male sterility line of rice, comprising:

introducing into a rice variety the restorer gene OsRf19 for cytoplasmic male sterility in rice of the first aspect or the nucleic acid of the third aspect or the expression vector of the fourth aspect to produce a transgenic restorer line; and crossing the transgenic restorer line with the cytoplasmic male sterility line to produce hybrid seeds having normal fertility.

In a seventh aspect, the present application provides use of the restorer gene OsRf19 for cytoplasmic male sterility in rice of the first aspect or the nucleic acid of the third aspect for rice breeding or creating a restorer line of rice or restoring fertility of a cytoplasmic male sterility line of rice.

In an eighth aspect, the present application provides a method of producing rice hybrid seeds, comprising: crossing a cytoplasmic male sterility line of rice as a female parent and a restorer line of rice comprising the restorer gene OsRf19 for cytoplasmic male sterility as a male parent to produce rice hybrid seeds, wherein the gene OsRf19 comprises the nucleotide sequence set forth in SEQ ID NO: 1 or comprises a nucleotide sequence encoding the amino acid sequence set forth in SEQ ID NO: 4.

BRIEF DESCRIPTION OF THE DRAWINGS

FIGS. 1A-1C show a map-based clone of the gene OsRf19 of the present application, in which FIG. 1A is a position of the OsRf19 on a genetic linkage map on chromosome 10 of rice; and FIGS. 1B and 1C utilize two mapping populations, respectively, to fine-position the OsRf19. The numbers between markers represent the number of recombination between each marker and the locus OsRf19.

FIGS. 3A-3E show a microscopic view of iodine staining of pollens and seed setting rate phenotypes of Tl transgenic plants of the present application, in which FIG. 3A is identification of transgenic plants by molecular markers; FIG. 3B shows the phenotypes of the entire plants of transgene negative (left) and transgene positive (right); FIG. 3C is the seed setting rate phenotype of transgene negative (left) and transgene positive spikelets (right); FIG. 3D is microscopic views of iodine staining of pollens of transgenic negative plants; and FIG. 3E is a microscopic view of pollens of transgenic positive plants.

FIGS. 4A-4B show the phenotypes of progenies of the OsRf19 transgenic positive plant of the present application after cross with a new cytoplasm derived sterility line 1A, in which FIG. 4A is the phenotype of iodine staining of pollens of the sterility line 1A (left) and $F_1$ plants (right) produced by crossing transgenic positive plants with the new cytoplasm derived sterility line; and FIG. 4B is spikelets of the sterility line 1A (left) and $F_1$ plants (right) produced by crossing transgenic positive plants with the new cytoplasm derived sterility line.

DETAILED DESCRIPTION

Definition

Figures 1A, 1B, 1C:
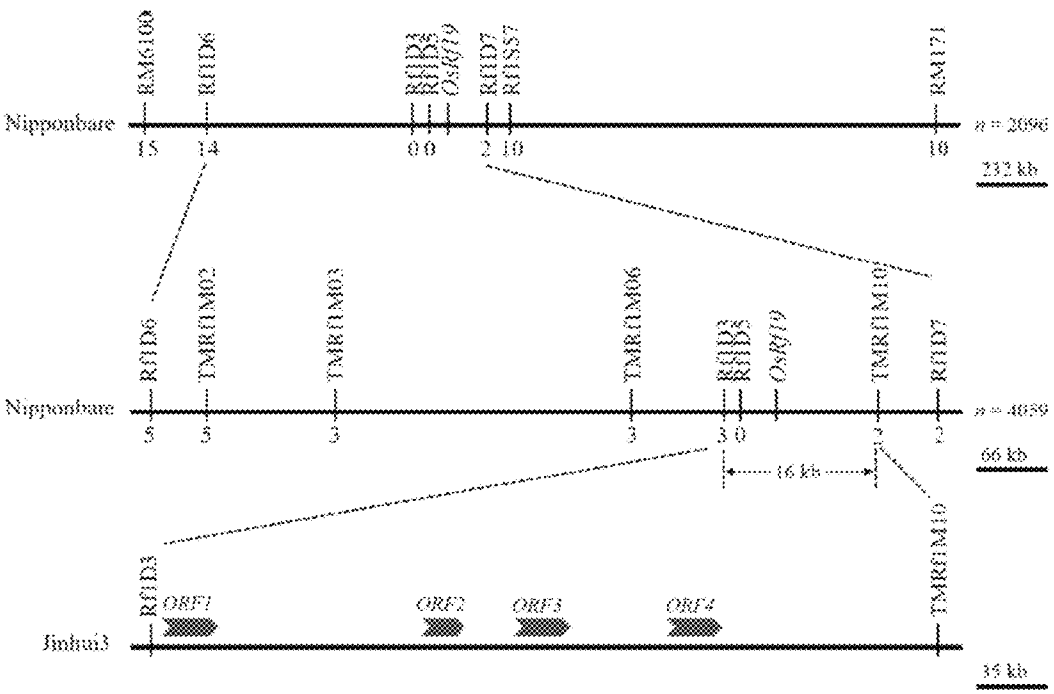

As used herein, "rice" is any rice plant and includes all plant varieties that can be bred with rice. As used herein, "plant" includes whole plants, plant cells, plant organs, plant protoplasts, plant cell tissue cultures from which plants can regenerate, plant calli, plant clumps, and intact plant cells in plants or plant parts such as embryos, pollens, ovules, seeds, leaves, flowers, branches, fruits, stems, roots, root tips, anthers, and the like. As used herein, rice includes *Oryza sativa*, upland rice, indica rice, japonica rice, early rice, late rice, viscous rice, glutinous rice, rice with hairy leaves, and rice without hairy leaves (naked rice) rice.

As used herein, the term "sterility line", also referred to as "male sterility line" or "cytoplasmic male sterility line", refers to a rice line that is pollen sterile and capable of passing on this characteristic to the progenies.

As used herein, the term "new cytoplasm derived sterility line (CMS-FA)" refers to a male sterility line developed from Fujian wild rice (*O. rufipogon*) and carrying the male sterile cytoplasm of Fujian wild rice, i.e., a sterility line having a specific CMS-FA cytoplasm background, referred to as CMS-FA or a new cytoplasmic sterility line. Since the utilization of its maintainer line resources reaches 55.5%, which is higher than 20% of the utilization of the maintainer line resources of the CMS-WA, it is also referred to as a cytoplasmic male sterility line of the Guangbao type, male sterility line of the Guangbao type, or a sterility line of the Guangbao type, for example, see Chinese Patent publication CN1954666B.

As used herein, the term "single nucleotide polymorphism" or "SNP" or "SNP marker" or "SNP site" refers to a nucleotide sequence present in the genomic sequence of a chromosome, a change in the polynucleotide sequence due to a difference in the nucleotide sequence (a change of a single nucleotide-A, T, C or G), resulting in diversity of the chromosomal genome, thereby allowing different alleles (e.g., alleles from two different individuals) or different individuals to distinguish from each other. This change may occur within the coding region or non-coding region of a gene (e.g., the promoter region or its vicinity, or within intron) or within the intergenic region.

As used herein, the term "InDel" refers to insertions or deletions, which specifically refer to differences in the entire genome, with a number of nucleotide insertions or deletions in the genome of the individual relative to a standard control (Jander et al., 2002).

As used herein, the term "SSR (Simple Sequence Repeats)", also known as microsatellite DNA, is a class of tandem repeats of up to several tens of nucleotides consisting of several nucleotides (typically 1 to 6) as repeating units. The sequences flanking each SSR are generally relatively conserved single copy sequences.

As used herein, the term "gene homologous to OsRf19" refers to a gene derived from the same species or a different species from rice OsRf19 and having a similar function.

As used herein, the term "gene editing" or "genome edting" is an emerging, more accurate, genetic engineering technique capable of modifying specific genes of interest in the genome of an organism. Gene editing refers to the ability to "edit" a gene of interest at a specific site to effect modification of a particular DNA fragment. Gene editing relies on genetically engineered nucleases, also known as "molecular scissors" that produce site-specific double-stranded breaks (DSBs) at specific locations in the genome, inducing an organism to repair the DSBs through non-homologous end joining (NHEJ) or homologous recombination (HR). As this repair process is error-prone, targeted mutations are produced.

As used herein, the term "CRISPR/Cas9" refers to an endonuclease that targets an endonuclease cleavage site using an RNA-guided strand. See, Jinek et al., Science 337:816-821 (2013); Cong et al., Science (Jan. 3, 2013); and Mali et al., Science (Jan. 3, 2013). The CRISPR/Cas9 systems currently found have three different types, i.e., types I, II and III, which are present in approximately 40% of the sequenced eubacteria and 90% of the sequenced archaeobacteria. The composition of the type II is relatively simple with Cas9 protein and gRNA as the core, and is the most thoroughly studied type at present. When bacteria resist foreign DNA intrusion, such as phages, under the control of the leader region, CRISPR is transcribed into long RNA precursors (pre-crRNA), which are then processed into a series of short mature crRNA containing conserved repeats and spacers, which ultimately recognize and bind to their complementary foreign DNA sequences for cleavage. The cleavage site of CRISPR/Cas9 is located at the NGG site in the 5'-GG-N18-NGG-3' feature region in the PAM region (Protospacer Adjacent Motif) adjacent downstream of the crRNA complementary sequence, and the sequences having such a feature is repeated once per 128 bp of random DNA sequence.

As used herein, the term "CRISPR/Cas12a" is a new type of CRISPR-Cas system. Cas12a protein is more accurate and safer than the Cas9 protein. When CRISPR/Cas9 works, the Cas9 protein recognizes the PAM sequence (the genetic code written by RNA) and uncoils the partial double helix by gRNA. In this process, the Cas9 protein will attached closely to the DNA as soon as a better matching sequence is found, and in this process, some mismatching may occur, but this binding is irreversible. In this respect, Cas12a uses a much smarter way to identify a single base along a DNA sequence when looking for a "target". If a mismatched base is found, it leaves and restart the search again. When a PAM sequence is found, the Cas12a protein forms a semi-closed R loop with the PAM sequence. When a correct sequence is recognized, the Cas12a protein will form a closed R loop, and therefore this binding is reversible and safer.

As used herein, the term "Transcriptional activator like effector nucleosidase", "TAL effector nucleosidase" or "TALEN" refers to a class of artificial restriction endonucleases produced by fusing a TAL effector DNA binding domain to a DNA cleavage domain.

As used herein, the term "zinc-finger nuclease (ZFN)" consists of a DNA recognition domain and a DNA cleavage domain. The DNA recognition domain is a 3 to 4 ZF tandem structure, each ZF containing about 30 amino acids, immobilized by a zinc ion, and capable of recognizing and binding a specific triplet base. The DNA cleavage domain consists of 96 amino acid residues at the carboxyl terminus of the non-specific endonuclease Fok I. Each Fok I monomer is linked to one ZFP to form one ZFN and recognizes a specific site. When two recognition sites are 6~8 bp from each other, two monomers ZFN interact to produce an enzyme cleavage function, forming a double-stranded cleavage, thereby mediating DNA site-directed cleavage.

As used herein, the term "meganuclease" refers to a homing endonuclease capable of recognizing a nucleic acid sequence of 14-40 base length. Some meganucleases can tolerate small differences in the homing site sequence, and large recognition regions can still guarantee the high specificity of these enzymes, which in turn can maintain non-specific cleavage within the genome and low levels of toxicity. Meganucleases are encoded by an open reading frame within a mobile sequence of a self-splicing RNA intron or self-splicing protein intron sequence.

As used herein, the term "DddA-derived cytosine base editor" is a new base editor created in 2020 by the research team led by the Bode Institute of Harvard University and Liu Ruqian of Massachusetts Institute of Technology, which can perform a C-to-T transition on DNA in mitochondria. This is accomplished by creating a new gene editing technique called base editing, which converts a single nucleotide base to another base without damaging the DNA. However, this technique also has its limitations. It is not limited only to the C-to-T conversion, but mainly to the TC motif, making it an effective TC-TT converter. This means that it can correct only 9 of the 90 identified pathogenic point mutations in mitochondria, i.e. 10%. The A-to-G conversion of mitochondrial DNA has long been considered impossible.

The term "transcriptional activator effect-related deaminase (TALED)" as used herein is a new gene editing platform developed by researchers at the Genome Engineering Center of the Korean Institute of Basic Science (IBS). TALED is a base editor capable of performing A-to-G base conversion in mitochondria. This discovery is the result of a decades-long journey to cure human genetic diseases. This new base editor greatly extends the scope of mitochondrial genome editing. This not only contributes significantly to the establishment of disease models, but also to the development of therapeutic methods. Notably, its ability to perform A to G transformation in human mtDNA can correct 39 of 90 known pathogenic mutations, approximately 43%. The researchers created TALED by combining three different components. The first component is the transcription activator-like effector, which is capable of targeting DNA sequences. The second component is TadA8e, an adenine deaminase for promoting A to G conversion. The third component, DddAtox, is a cytosine deaminase that makes DNA more readily available by TadA8e.

Specific Embodiments

The present application provides the nucleotide sequence of the OsRf19 gene and the encoded protein thereof. The nucleotide sequence is shown in SEQ ID NOs: 1, 2 and 3 in the Sequence Listing, wherein SEQ ID NO:1 is an open reading frame (ORF) of 2376 bases without introns, SEQ ID NO: 2 is a sequence containing the promoter control element and the 5' untranslated region, and SEQ ID NO:3 is the sequence of the 3' untranslated region. The sequence of the protein encoded by the gene OsRf19 is shown in SEQ ID NO:4. This sequence consists of 791 amino acids and has a functional domain consisting of 19 PPR repeating units (pentatricopeptide repeat) whose biological function is to restore the fertility of plant cytoplasmic male sterility. A typical PPR is a repeating unit consisting of 35 amino acid residues, and a functional domain is formed from two or more PPR units in the same direction in different PPR-containing proteins. The amino acid sequences of different PPR units have a certain difference.

In particular, the present application relates to the following technical solutions.

In a first aspect, the present application provides a restorer gene OsRf19 for cytoplasmic male sterility in rice comprising the nucleotide sequence set forth in SEQ ID NO: 1 or a functional variant thereof.

SEQ ID NO: 1 is an open reading frame of 2376 bases without introns. Those skilled in the art will be able to identify and/or obtain functional variants of the restorer gene OsRf19 for cytoplasmic male sterility in rice via conventional methods. The functional variants may have deletions, additions and/or substitutions of one or more nucleotides as compared to the original gene, but still retain the function of the original gene, for example a variant still encoding proteins having the same function. The functional variant may have at least about 70%, 75%, 80%, 85%, 86%, 87%, 88%, 89%, 90%, 91%, 92%, 93%, 94%, 95%, 96%, 97%, 98%, 99% or more sequence identity to the sequence set forth in SEQ ID NO: 1 and encodes a protein having the same function. Thus, SEQ ID NO: 1 includes both the nucleotide sequence set forth in SEQ ID NO: 1 itself and functional variants of the nucleotide sequence set forth in SEQ ID NO: 1.

As used herein, the term "functional variant" refers to a substantially similar sequence. For nucleotide sequences, functional variants include those sequences that encode proteins having the same function due to degeneracy of the genetic codon. Naturally occurring allelic variants may be identified using well-known molecular biology techniques such as polymerase chain reaction (PCR) and hybridization techniques. For example, in the present application, genes derived from other rice varieties having at least about 70%, 75%, 80%, 85%, 86%, 87%, 88%, 89%, 90%, 91%, 92%, 93%, 94%, 95%, 96%, 97%, 98%, 99% or more identity to the gene OsRf19 and also encoding a functional OsRf19 protein are included in "functional variants" as defined herein. Identity is determined by the sequence alignment program described herein with default parameters. The sequences of the functional variants of a nucleotide may differ from the nucleotide sequence by as few as 1 to 15 nucleotides, as few as 1 to 10 (e.g., 6 to 10), as few as 5, as few as 4, 3, 2 or even 1 nucleotide.

According to the sequence information of the gene OsRf19 provided in the present application, genes homologous to OsRf19 or functional variants of OsRf19 can be readily obtained by (a) obtaining homologous genes of OsRf19 that have been disclosed but are not known in function by comparison with a database; (b) screening the rice genome library using a fragment of the gene OsRf19 as a probe to obtain positive clones and sequencing; (c) designing oligonucleotide primers based on the sequence information of SEQ ID NO:1, amplifying OsRf19 gene fragments from the genome of rice or wild-type rice by PCR and sequencing; (d) molecular biologically modifying the sequence of SEQ ID NO: 1; or (e) chemical synthesis with reference to the sequence of SEQ ID NO:1.

In some embodiments, the restorer gene OsRf19 for cytoplasmic male sterility in rice consists of SEQ ID NOs: 1, 2 and 3, wherein SEQ ID NO: 1 is an open reading frame (ORF) of 2376 bases without introns, SEQ ID NO: 2 is a sequence containing the promoter control element and the 5' untranslated region, and SEQ ID NO:3 is the sequence of the 3' untranslated region.

In a preferred embodiment, the restorer gene OsRf19 for cytoplasmic male sterility in rice consists of SEQ ID NO: 1.

In a second aspect, the present application provides a protein encoded by the restorer gene OsRf19 for cytoplasmic male sterility in rice and comprising or consisting of the amino acid sequence set forth in SEQ ID NO: 4, or a functional variant thereof.

Those skilled in the art will be able to identify and/or obtain the functional variants via conventional methods. The functional variants may have deletions, additions and/or substitutions (e.g., conservative substitutions) of one or more amino acids as compared to the original protein, but still retain the function of the original protein, for example the function to restore the fertility of the cytoplasmic male sterility line of rice. The functional variant may have at least about 70%, 75%, 80%, 85%, 86%, 87%, 88%, 89%, 90%, 91%, 92%, 93%, 94%, 95%, 96%, 97%, 98%, 99% or more sequence identity to the sequence set forth in SEQ ID NO: 4 and retain the function of the original protein. Thus, SEQ ID NO: 4 includes both the amino acid sequence set forth in SEQ ID NO: 4 itself and the functional variants of the amino acid sequence set forth in SEQ ID NO: 4.

For a protein sequence, the term "functional variant" includes polypeptides derived from a natural protein by deletion (so-called truncation) of one or more amino acids at the N-terminus and/or C-terminus of the natural protein or by addition of one or more amino acids to the N-terminus and/or C-terminus of the natural protein; by deletion or addition of one or more amino acids at one or more sites of the native protein; or by substitution of one or more amino acids at one or more positions of the native protein. Thus, in the case of a protein, the term "functional variant" includes a biologically active fragment of a natural protein containing a sufficient number of contiguous amino acid residues that retain the biological activity of the natural protein, e.g., the function of the OsRf19 protein. Such functions may be different or modified with respect to the native protein, or may be unchanged as long as the function of the OsRf19 protein is preserved. Identity is determined by the sequence alignment program described herein with default parameters. The active variant sequence of a protein may differ from the protein by as few as 1 to 15 amino acid residues, as few as 1 to 10 (e.g., 6 to 10), as few as 5, as few as 4, 3, 2 or even 1 amino acid residue.

In a particular embodiment, the protein consists of the amino acid sequence set forth in SEQ ID NO: 4.

In a third aspect, the present application provides a nucleic acid encoding the protein of the second aspect.

In a preferred embodiment, the nucleic acid may be a codon optimized nucleic acid suitable for expression in host cells. For example, according to the degeneracy of the codon, it still encodes the same protein. Methods for codon optimization according to the host cells used are well known to those skilled in the art.

In a fourth aspect, the present application provides an expression vector comprising the restorer gene OsRf19 for cytoplasmic male sterility in rice of the first aspect or the nucleic acid of the third aspect.

Any suitable expression vector may be used. For example, prokaryotic cloning vectors include plasmids from *E. coli*, such as colEl, pCRI, pBR322, pMB9, pUC, pKSM, and RP4. Prokaryotic vectors also include phage DNA such as M13 and other derivatives of filamentous single-stranded DNA phages. An example of a vector useful for yeast is the 2μ plasmid. Suitable vectors for expression in mammal cells include the following well-known derivatives: SV-40, adenovirus, retrovirus-derived DNA sequences, and shuttle vectors derived from combinations of functional mammal vectors, such as those described above, and functional plasmids and phage DNA.

Additional eukaryotic expression vectors are known in the art (e.g., P J. Southern & P. Berg, J. Mol. Appl. Genet, 1:327-341 (1982); Subramani et al., Mol. Cell. Biol, 1:854-864 (1981); Kaufinann & Sharp, "Amplification And Expression of Sequences Cotransfected with a Modular Dihydrofolate Reductase Complementary DNA Gene," J. Mol. Biol, 159:601-621 (1982); Kaufhiann & Sharp, Mol. Cell. Biol, 159:601-664 (1982); Scahill et al., "Expression And Characterization Of The Product Of A Human Immune Interferon DNA Gene In Chinese Hamster Ovary Cells," Proc. Nat'l Acad. Sci USA, 80:4654-4659 (1983); Urlaub & Chasin, Proc. Nat'l Acad. Sci USA, 77:4216-4220, (1980), which are incorporated herein by reference in their entirety).

Expression vectors useful in the present invention contain at least one expression control sequence operably linked to a DNA sequence or fragment to be expressed. The control sequence is inserted into a vector to control and regulate the expression of cloned DNA sequences. Examples of useful expression control sequences are the lac system, the trp system, the tac system, the trc system, the major operons and promoter region of the phage Lamda, the control region of the fd coat protein, the glycolytic promoter of the yeast such as the promoter of 3-phosphoglycerate kinase, the promoter of the yeast acid phosphatase such as Pho5, the promoter of the yeast Alpha-mating factor, and promoters derived from polyomavirus, adenovirus, retrovirus, and simian virus such as the early and late promoters of SV40, and other sequences known to control gene expression of prokaryotic or eukaryotic cells and viruses or combinations thereof.

In a fifth aspect, the present application provides a method of creating a restorer line of rice, which comprises introducing into a rice variety the restorer gene OsRf19 for cytoplasmic male sterility in rice of the first aspect or the nucleic acid of the third aspect or the expression vector of the fourth aspect.

In some embodiments, the introduction is carried out by gene editing.

In some embodiments, the rice variety is selected from the group consisting of *Oryza sativa*, upland rice, indica rice, japonica rice, early rice, late rice, viscous rice, glutinous rice, rice with hairy leaves, and rice without hairy leaves.

In some embodiments, the gene editing is carried out by one or more selected from the group consisting of CRISPR/Cas9, CRISPR/Cpf1, CRISPR/Cas12a, TALEN, meganuclease, ZFN, DddA derived cytosine base editors, and TALED. Preferably, the gene editing is carried out by CRISPR/Cas9.

In a sixth aspect, the present application provides a method of restoring the fertility of a cytoplasmic male sterility line of rice, comprising:

- introducing into a rice variety the restorer gene OsRf19 for cytoplasmic male sterility in rice of the first aspect or the nucleic acid of the third aspect or the expression vector of the fourth aspect to produce a transgenic restorer line; and
- crossing the transgenic restorer line with the cytoplasmic male sterility line to produce hybrid seeds having normal fertility.

In some embodiments, the cytoplasmic male sterility line of rice is a new cytoplasm derived sterility line. Specifically, the cytoplasmic male sterility line of rice is a sterility line of rice containing the sterility gene orf182.

In a specific embodiment, the sterility line of rice employed is a new cytoplasm derived sterility line containing the mitochondrial sterility gene orf182. The new cytoplasm derived sterility line containing the mitochondrial sterility gene orf182 is a sporophytic sterility line, which has no pollen abortion, complete abortion and extremely stable fertility. The sequence of the mitochondrial sterility gene orf182 is shown in SEQ ID NO: 9.

In some embodiments, the introduction is carried out by gene editing.

In some embodiments, the rice variety and the cytoplasmic male sterility line of rice are each selected from the group consisting of *Oryza sativa*, upland rice, indica rice, japonica rice, early rice, late rice, viscous rice, glutinous rice, rice with hairy leaves, and rice without hairy leaves.

In some embodiments, the gene editing is carried out by one or more selected from the group consisting of CRISPR/Cas9, CRISPR/Cpf1, CRISPR/Cas12a, TALEN, meganuclease, ZFN, DddA derived cytosine base editors, and TALED. Preferably, the gene editing is carried out by CRISPR/Cas9.

In a seventh aspect, the present application provides use of the restorer gene OsRf19 for cytoplasmic male sterility in rice of the first aspect or the nucleic acid of the third aspect for rice breeding or creating a restorer line of rice or restoring fertility of a cytoplasmic male sterility line of rice.

In some embodiments, the cytoplasmic male sterility line of rice is a new cytoplasm derived sterility line. Specifically, the cytoplasmic male sterility line of rice is a sterility line of rice containing the sterility gene orf182.

In a specific embodiment, the sterility line of rice employed is a new cytoplasm derived sterility line containing the mitochondrial sterility gene orf182. Specifically, the sterility gene orf182 comprises the nucleotide sequence set forth in SEQ ID NO: 9.

The OsRf19-like gene described in the present application is defined as a gene having one or several nucleotide differences compared to the nucleotide sequence of SEQ ID NO: 1, including changes, deletions, or insertions of several bases, and expressing a product, the function of which is equivalent to the function of the expression product of OsRf19.

In an eighth aspect, the present application provides a method of producing rice hybrid seeds, comprising: crossing a cytoplasmic male sterility line of rice as a female parent and a restorer line of rice comprising the restorer gene OsRf19 for cytoplasmic male sterility as a male parent to produce rice hybrid seeds, wherein the gene OsRf19 comprises the nucleotide sequence set forth in SEQ ID NO: 1 or comprises a nucleotide sequence encoding the amino acid sequence set forth in SEQ ID NO: 4.

In some embodiments, the cytoplasmic male sterility line of rice is a new cytoplasm derived sterility line. Specifically, the cytoplasmic male sterility line of rice is a sterility line of rice containing the sterility gene orf182.

In a specific embodiment, the sterility line of rice employed is a new cytoplasm derived sterility line containing the mitochondrial sterility gene orf182. Specifically, the sterility gene orf182 comprises the nucleotide sequence set forth in SEQ ID NO: 9.

In some embodiments, the restorer line of rice and the cytoplasmic male sterility line of rice are each selected from the group consisting of *Oryza sativa*, upland rice, indica rice, japonica rice, early rice, late rice, viscous rice, glutinous rice, rice with hairy leaves, and rice without hairy leaves.

The terms "including", "comprising", and "containing" mean "including but not limited to", and are not intended to exclude other parts, additions, components or steps.

It is to be understood that features, characteristics, components, or steps described in a particular aspect, embodiment, or example of the present application may be applied to any other aspect, embodiment, or example described herein unless contradicted thereby.

EXAMPLES

The following examples are for purposes of illustration only and are not intended to limit the scope of the present application.

The information about the rice plant material used in the present application can be found in the Chinese rice varieties and their pedigree database (http://www.ricedata.cn/variety/index.htm).

Example 1: Preliminary Mapping of Restorer Gene OsRf19 (Also Known as RFFA) for New Cytoplasm Derived Male Sterility in Rice Studies have shown that the new cytoplasm derived sterility line (CMS-FA) produces normally fertile $F_1$ generation by crossing with a restorer line, and that the fertility restorer (fertile) gene is predominantly inherited. The ratio of fertility lines and sterility lines isolated from the $F_2$ generation is 3:1, and fertility recovery (fertility) gene is controlled by a pair of dominant genes (Wang Naiyuan et al., 2008b). The three-line hybrid rice Jinnong 2 You 3 (see Chinese rice varieties and their pedigree database website: https://www.ricedata.cn/variety/varis/605314.htm) has the female parent of the male sterility line Jinnong 2A (see Chinese rice varieties and their pedigree database website: https://www.ricedata.cn/variety/varis/607151.htm), and the male parent of the restorer line Jinhui 3 (see Chinese rice varieties and their pedigree database website: https://www.ricedata.cn/variety/varis/609760.htm). Jinnong 2A is a new cytoplasm derived sterility line (CMS-FA) and Jinhui 3 is a CMS-FA restorer line containing a CMS-FA restorer gene designated OsRf19 in rice. In order to clone this gene, the inventors planted about 2000 plants of self-bred progeny ($F_2$ progeny) population of Jinnong 2 You 3 in Sanya base of Hainan province. The fertility of 94 plants was investigated and found that 74 plants were fertile and 20 plants were sterile, which was consistent with 3:1 ($x^2$=0.695, P=0.405), indicating the single gene dominant inheritance. The genomic DNA was extracted from the leaves of 10 fertile plants (fertile pool) and 20 sterile plants (sterile pool) randomly selected from a population of 2000 plants. The genomic DNA was grouped and analyzed using a RICE6K rice whole genome breeding chip (CN 102747138A) (BSA, Bulked Segregant Analysis). The results showed that the major genotype difference between fertile pool and sterile pool was about 1800 kb region of 18.1-19.9 Mb on chromosome 10 (Chr10) of rice, containing the cloned CMS restorer genes Rfla and Rflb (Wang et al, 2006). In this region, the polymorphism SNP genotype of the fertile pool is heterozygous, while the genotype of the sterile pool is homozygous, indicating that the fertility is dominant.

Example 2: Fine Mapping of the Restorer Gene OsRf19 for New Cytoplasm Derived Male Sterility in Rice In order to develop and utilize more molecular markers to finely map the OsRf19 gene, SSR markers (http://www-.gramene.org/) in the public database were used, while genome-wide sequencing (http://www.illumina.com/) of the parents Jinnong 2A and Jinhui 3 was performed using Illumina next generation sequencing techniques, and SSR, InDel and SNP markers were obtained by sequence alignment. The materials used for mapping were populations of 2096 $F_2$ plants and its self-bred progenies $F_3$ and $F_4$ from Jinnong 2 You 3 for prelimitary mapping. Cloning mapping was used for mapping it to a region of about 66 Kb between two molecular markers, Rf1D6 (Chr10: 18.828 Mb) and Rf1D7 (Chr10: 18.894 Mb) (rice TIGR/MSU Note, version 6.1, http://rice.plantbiology.msu.edu/), containing Rfla and not containing Rflb (FIGS. 1A-1C). Subsequently, a total of 4059 individual plants of $BC_1F_2$ and $BC_2F_2$ progenies, which were obtained by crossing Jinhui 3 with Huazhan (see Chinese rice varieties and their pedigree database website: https://www.ricedata.cn/variety/varis/607962.htm) and then using Huazhan as a recurrent parent, were further for mapping of the restorer gene, which was mapped to a region of about 16 Kb between the molecular markers Rf1D3 (18.874 Mb) and TMRf1M10 (18.890 Mb) (rice TIGR/MSU Note, version 6.1, http://rice.plantbiology.msu.edu/).

Example 3: Construction of Whole Genome BAC Library of Rice Jinhui 3 and Sequencing of Target BAC In order to obtain more accurate information on the mapping, we constructed a whole genome BAC library of the rice restorer line variety Jinhui 3. The total number of clones in the BAC library was 41472, and the average insert size was about 114 kb, covering about 10.5 times the rice genome. Two fragments BAC 71-N-20 and 90-J-22 containing the target region were screened in the BAC library using the linkage markers for mapping the region. The two BAC fragments were subsequently sequenced and analyzed, and four candidate genes ORF1, ORF2, ORF3 and ORF4 were predicted between localizer markers Rf1D3 and TMRf1M10 (FIGS. 1A-1C). Since the transgene complementarity of ORF2, ORF3 and ORF4 had no phenotypes, clone ORF1 was the only reliable candidate gene for OsRf19.

SEQ ID NO:1 is an open reading frame (ORF) of 2376 bases without introns derived from the OsRf19 gene isolated and cloned from the rice Jinhui 3.

SEQ ID NO: 2 is a sequence containing the promoter control element and a 5' untranslated region of the OsRf19 gene.

SEQ ID NO:3 is the sequence of the 3' untranslated region of the OsRf19 gene.

SEQ ID NO:4 is an amino acid sequence of the OsRf19 gene isolated and cloned from the rice Jinhui 3.

Example 4: Creation of New Cytoplasm Derived Sterility Line 93-11A in Rice

In order to obtain a stable sterility line material for subsequent transgenic complementarity experiments, $F_1$ hybrids were obtained by crossing Jinnong 2A as a female parent with indica rice variety 93-11 (see Chinese rice varieties and their pedigree database website: https://www.ricedata.cn/variety/varis/600611.htm) as a male parent. $BC_7F_1$ plants were then obtained after successive back-crosses with the hybrids for 7 generations using the variety 93-11 as the recurrent parent. A material, in which the nuclear genomic DNA is substantially identical to the variety 93-11, but the cytoplasm of Jinnong 2A is retained, was obtained after backcross, and this rice material was named as a new rice 93-11A. The variety 93-11 and new rice 93-11A at flowering and maturation were investigated for phenotype. The results revealed that the pollens from 93-11 were fertile and pollens from the new rice 93-11A were sterile by iodine staining; 93-11 had normal seed setting at ripening, but the new rice 93-11A could not produce seeds at ripening with a seed setting rate of 0. We have obtained a stable sterility line material 93-11A via the above methods.

The seeds of the sterility line of rice 93-11A (which contains the sterility gene orf182) obtained in this example were deposited on China Center for Type Culture Collection at Wuhan University, Wuhan, China with the following information on Jul. 28, 2021:

Deposition institution: China Center for Type Culture Collection (CCTCC)
Address: Wuhan University, Wuhan, Hubei, China
Date of deposit: Jul. 28, 2021
Culture Name (Taxonomic Nomenclature): *Oryza sativa* Seed Xinzhi 93-11A
Accession number: CCTCC NO: P202115.

A deposit of Huazhong Agricultural University and China National Seed Group Corporation, Ltd. proprietary seeds of the sterility line disclosed above and recited in the appended claims has been made with the China Center for Type Culture Collection (CCTCC) (Wuhan University, Wuhan, China) and has been accepted under the terms of the Budapest Treaty. The date of deposit was Jul. 28, 2021. The deposit of 2,000 seeds was taken from the same deposit maintained by the Huazhong Agricultural University (No. 1, Shizishan Street, Hongshan District, Wuhan, Hubei 430070, China) and China National Seed Group Corporation, Ltd. (17/F You'an International Building, Xitieying Middle Road, Fengtai District, Beijing 100069, China) since prior to the filing date of this application. The CCTCC Accession Number is P202115. The deposit will be maintained in the depository for a period of thirty years, or five years after the last request, or for the enforceable life of the patent, whichever is longer, and will be replaced as necessary during that period. All restrictions upon availability of the biological material to the public will be irrevocably removed upon granting of the patent for the enforceable life of the patent in accordance with 37 CFR § 1.808(a)(2), and the deposit is intended to meet all of the requirements of 37 CFR. §§ 1.801-1.809.

Example 5: Transgenic Complementarity Assay for OsRf19

A pair of PCR amplification oligonucleotide primers with restriction endonuclease BamHI and PstI linkers were designed based on the predicted full-length sequence of the candidate gene, with the primer sequences shown in SEQ ID NO:5 (with the cutting site of restriction endonuclease BamHI underlined) and SEQ ID NO:6 (with the cutting site of restriction endonuclease PstI underlined).

```
SEQ ID NO: 5:
5'-GAGCTCGGTACCCGGGGATCCTCGGTCCCGTATTTTGAATC-3'

SEQ ID NO: 6:
5'-GCCAAGCTTGCATGCCTGCAGTAGAAGAGCAGCTGCACCAA-3'
```

Figure 2:
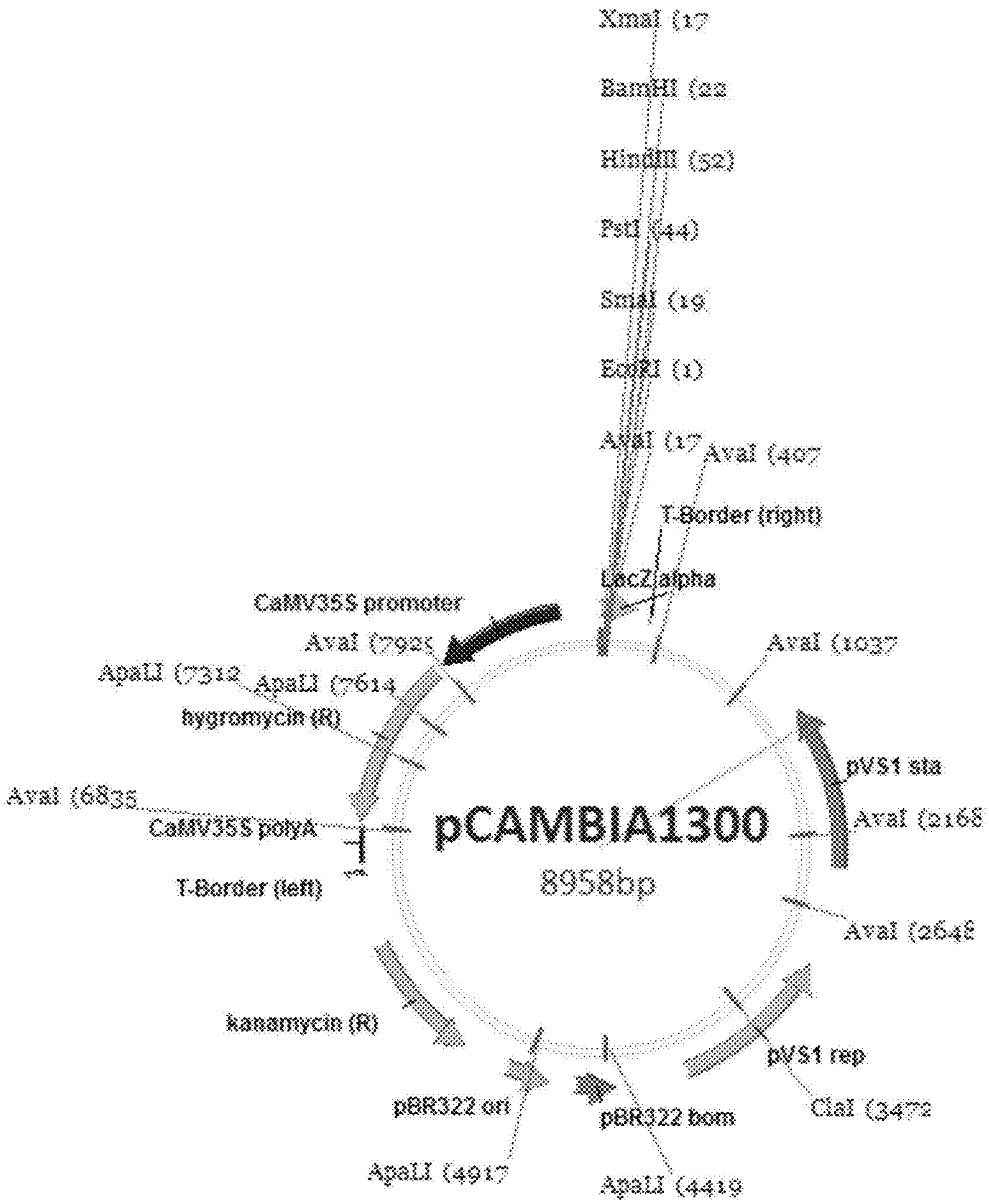
FIG. 2 is a vector map of the OsRf19 transgene complementarity verification of the present application, i.e., the map of the functional vector pCAMBIA1300 used.
Figures 3A, 3B, 3C, 3D, 3E:
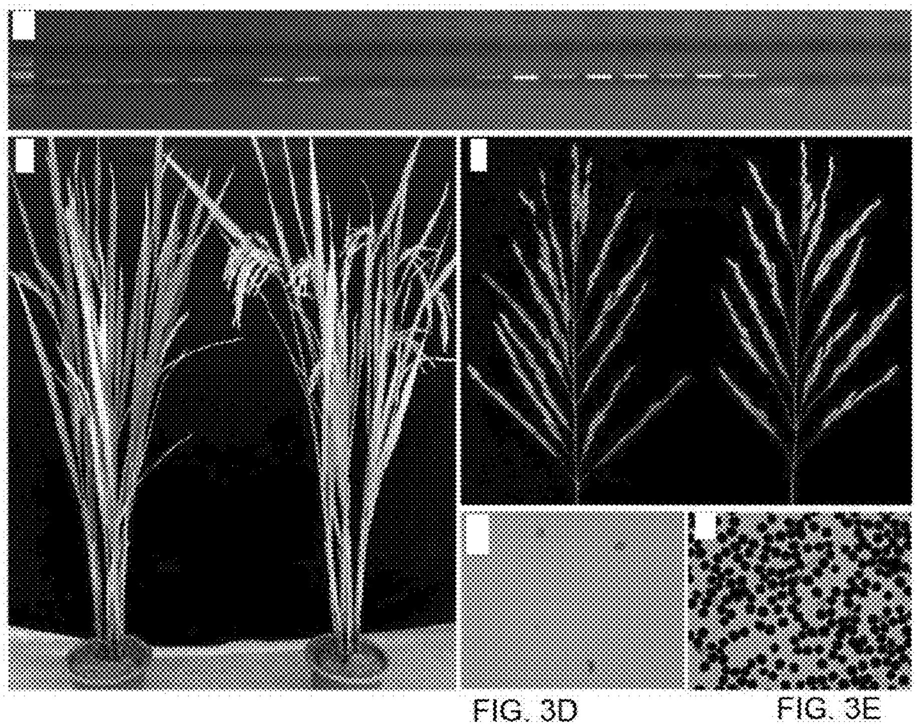

A fragment of 5071 bp in length containing a promoter, a coding region and a downstream termination sequence was amplified by PCR from a subclone of Jinhui 3. The PCR reaction system was as follows: 1× reaction buffer, 200 μM of dNTPs, 100 ng of subcloned DNA, primer each 0.3 μM, KOD FX polymerase 1.0 U were contained in a 50 μl reaction. Reaction procedure was as follows: step 1:95° C. 5 min; step 2:95° C. 20S, 55° C. 30S, 72° C. 5 min (30 cycles); step 3:72° C. 7 min; step 4:25° C. 1 min. After completion of the reaction, the PCR product was purified. After cleavage of the vector pCAMBIA1300 (CAMBIA, Canberra, Australia, FIG. 2) with restriction enzymes BamHI and PstI, the PCR product, which was also cleaved by restriction enzymes BamHI and PstI, was ligated to the vector. The correct cloning vector without mutation was selected and introduced into *Agrobacterium* EHA105. Calli were induced from mature seeds of new cytoplasm derived sterility line of rice 93-11A on induction medium. Transgenic rice plantlets were obtained by transfecting calli from 93-11A with EHA105 comprising vector transformed with the target gene, co-culturing and selecting calli with hygromycin resistance, differentiation, rooting, and plantlet transplanting.

The steps of the genetic transformation, culture medium and preparation method thereof are as follows:

(1) Reagent and Solution Abbreviations

The abbreviations for reagents and phytohormones used in the medium are as follows: 6-BA (6-BenzylaminoPurine); CN (Carbenicillin); KT (Kinetin); NAA (Napthalene acetic acid); IAA (Indole-3-acetic acid); 2,4-D (2,4-dichlorophenoxyacetic acid); AS (Acetosringone); CH (Casein Enzymatic Hydrolysate); HN (Hygromycin B); DMSO (Dimethyl Sulfoxide); $N6_{max}$ (N6 major element component solution); $N6_{mix}$ (N6 trace element component solution); $MS_{max}$ (MS major element component solution); $MS_{mix}$ (MS trace element component solution)

(2) Solution Formulation

1) Stock Solution of Major Elements of $N6_{Max}$ Medium (Prepared According to 10-Fold Concentrate (10×)):

| | |
|---|---|
| Potassium nitrate ($KNO_3$) | 28.3 g |
| Potassium dihydrogen phosphate ($KH_2PO_4$) | 4.0 g |
| Ammonium sulfate ($(NH_4)_2SO_4$) | 4.63 g |
| Magnesium sulfate ($MgSO_4$•$7H_2O$) | 1.85 g |
| Calcium chloride ($CaCl_2$•$2H_2O$) | 1.66 g or $CaCl_2$ 1.25 g |

The reagents were dissolved one by one, then made up to 1000 ml with distilled water at room temperature and stored at room temperature.

2) Stock Solution of Trace Elements of N6 Min Medium (Prepared According to 100-Fold Concentrate (100×)):

| | |
|---|---|
| Potassium iodide (KI) | 0.08 g |
| Boric acid ($H_3BO_3$) | 0.16 g |
| Manganese sulfate ($MnSO_4$•$4H_2O$) | 0.44 g or MnSO4•$2H_2O$ 0.3335 g |
| Zinc sulfate ($ZnSO_4$•$7H_2O$) | 0.15 g |

The reagents were dissolved at room temperature and made up to 1000 ml with distilled water and stored at room temperature.

3) Stock Solution of Ferric Salt ($Fe^{2+}$EDTA) (Prepared According to 100× Concentrate):

3.73 g of disodium ethylenediammonium tetraacetate ($Na_2EDTA·2H_2O$) and 2.78 g of $FeSO_4·7H_2O$ were dissolved respectively, mixed and made up to 1000 ml with distilled water, and incubated at 70° C. for 2 hours, and stored at 4° C. for later use.

4) Stock Solution of Vitamin (Prepared According to 100× Concentrate):

| | |
|---|---|
| Nicotinic acid | 0.1 g |
| Vitamin B1 (Thiamine HCl) | 0.1 g |
| Vitamin B6 (Pyridoxine HCl) | 0.1 g |
| Glycine | 0.2 g |
| Inositol | 10 g |

They were made up to 1000 ml with distilled water and store at 4° C. for later use.

5) Stock Solution of Major Elements of MS Medium ($MS_{max}$ Stock) (Prepared According to 10× Concentrate):

| | |
|---|---|
| Ammonium nitrate ($NH_4NO_3$) | 16.5 g |
| Potassium nitrate ($KNO_3$) | 19.0 g |
| Potassium dihydrogen phosphate ($KH_2PO_4$) | 1.7 g |
| Magnesium sulfate ($MgSO_4$•$7H_2O$) | 3.7 g |
| Calcium chloride ($CaCl_2$•$2H_2O$) | 4.4 g |

The reagents were dissolved at room temperature and made up to 1000 ml with distilled water and stored at room temperature.

6) Stock Solution of Trace Elements of MS Medium ($MS_{min}$ Stock) (Prepared According to 100× Concentrate):

| | |
|---|---|
| Manganese sulfate ($MnSO_4$•$4H_2O$) | 2.23 g |
| Zinc sulfate ($ZnSO_4$•$7H_2O$) | 0.86 g |
| Boric acid ($H_3BO_3$) | 0.62 g |
| Potassium iodide (KI) | 0.083 g |
| Sodium molybdate ($Na_2MoO_4$•$2H_2O$) | 0.025 g |
| Copper sulfate ($CuSO_4$•$5H_2O$) | 0.0025 g |
| Cobalt chloride ($CoCl_2$•$6H_2O$) | 0.0025 g |

The reagents were dissolved at room temperature and made up to 1000 ml with distilled water and stored at room temperature.

7) Preparation of 2,4-D Stock Solution (1 mg/Ml):

100 mg of 2,4-D was dissolved in 1 ml of 1 N potassium hydroxide for 5 minutes, and then 10 ml of distilled water was added for complete dissolution. The mixture was made up to 100 ml with distilled water and stored at room temperature.

8) Preparation of 6-BA Stock Solution (1 mg/Ml):

100 mg of 6-BA was dissolved in 1 ml of 1 N potassium hydroxide for 5 minutes, then 10 ml of distilled water was added for complete dissolution. The mixture was made up to 100 ml with distilled water and stored at room temperature.

9) Preparation of NAA Stock Solution (1 mg/Ml):

100 mg of NAA was dissolved in 1 ml of 1 N potassium hydroxide for 5 minutes, then 10 ml of distilled water was added for complete dissolution. The mixture was made up to 100 ml with distilled water and stored at 4° C. in the dark.

10) Preparation of IAA Stock Solution (1 mg/Ml):

100 mg of IAA was dissolved in 1 ml of 1 N potassium hydroxide for 5 minutes, then 10 ml of distilled water was added for complete dissolution. The mixture was made up to 100 ml with distilled water and stored at 4° C. in the dark.

11) Preparation of Glucose Stock Solution (0.5 g/Ml):

125 g of glucose was dissolved in distilled water to a volume of 250 ml and stored at 4° C. after sterilization.

12) Preparation of AS Stock Solution:

0.392 g of AS was dissolved in 10 ml of DMSO, aliquoted into a 1.5 ml centrifuge tube, and stored at −20° C. for later use.

13) Preparation of 1 N Potassium Hydroxide Stock Solution:

5.6 g of potassium hydroxide was dissolved in distilled water to a volume of 100 ml, and stored at room temperature for later use.

(3) Medium Formulation for Genetic Transformation of Rice:

1) Induction Medium

| | |
|---|---|
| $N6_{max}$ stock solution (10X concentrate as prepared, the same below) | 100 ml |
| $N6_{mix}$ stock solution (100X concentrate as prepared, the same below) | 10 ml |
| $Fe^{2+}$EDTA stock solution (100X concentrate as prepared, the same below) | 10 ml |
| Vitamin stock solution (100X concentrate as prepared, the same below) | 10 ml |
| 2,4-D stock solution (prepared above) | 2.5 ml |
| Proline | 0.3 g |
| CH | 0.6 g |
| Sucrose | 30 g |
| Phytagel (separately added, to be dissolved by heating, the same below) | 3 g |

They were added to 900 ml with distilled water, and the pH was adjusted to 5.9 with 1 N potassium hydroxide. The solution was boiled and made up to 1000 ml, aliquoted into a 50 ml triangular flask (30 ml/flask), and sterilized by conventional methods after sealing (for example, sterilization at 121° C. for 15 minutes, the following sterilization method for medium is the same as this).

2) Subculture Medium:

| | |
|---|---|
| $N6_{max}$ stock solution (10X) | 100 ml |
| $N6_{mix}$ stock solution (100X) | 10 ml |
| $Fe^{2+}$EDTA stock solution (100X) | 10 ml |
| Vitamin stock solution (100X) | 10 ml |
| 2,4-D stock solution | 2.0 ml |
| Proline | 0.5 g |
| CH | 0.6 g |

-continued

| | |
|---|---|
| Sucrose | 30 g |
| Phytagel | 3 g |

They were added to 900 ml with distilled water, and the pH was adjusted to 5.9 with 1 N potassium hydroxide. The solution was boiled and made up to 1000 ml, aliquoted into a 50 ml triangular flask (30 ml/flask), sealed, and sterilized as described above.

3) Pre-Culture Medium (Japonica Rice without this Step):

| | |
|---|---|
| $N6_{max}$ stock solution (10X) | 12.5 ml |
| $N6_{mix}$ stock solution (100X) | 1.25 ml |
| $Fe^{2+}$EDTA stock solution (100X) | 2.5 ml |
| Vitamin storage solution (100X) | 2.5 ml |
| 2,4-D stock solution | 0.75 ml |
| CH | 0.15 g |
| Sucrose | 5 g |
| Agar powder | 1.75 g |

They were added to 250 ml with distilled water, and the pH was adjusted to 5.6 with 1 N potassium hydroxide. The solution was sealed, and sterilized as described above.

The medium was dissolved by heating prior to use and 5 ml of glucose stock solution and 250 µl of AS stock solution were added, and the aliquots were poured into petri dishes (25 ml/dish).

4) Suspension Medium:

| | |
|---|---|
| $N6_{max}$ stock solution (10X) | 5 ml |
| $N6_{mix}$ stock solution (100X) | 0.5 ml |
| $Fe^{2+}$EDTA stock solution (100X) | 0.5 ml |
| Vitamin storage solution (100X) | 1 ml |
| 2,4-D stock solution | 0.2 ml |
| CH | 0.08 g |
| Sucrose | 2 g |

They were added to 100 ml with distilled water, and the pH was adjusted to 5.4. The solution was split into two 100 ml flasks, sealed, and sterilized as described above.

1 ml of sterile glucose stock solution and 100 µl of AS stock solution were added prior to use.

5) Co-Culture Medium:

| | |
|---|---|
| $N6_{max}$ stock solution (10X) | 12.5 ml |
| $N6_{mix}$ stock solution (100X) | 1.25 ml |
| $Fe_{2+}$EDTA stock solution (100X) | 2.5 ml |
| Vitamin storage solution (100X) | 2.5 ml |
| 2,4-D stock solution | 0.75 ml |
| CH | 0.2 g |
| Sucrose | 5 g |
| Agar powder | 1.75 g |

They were added to 250 ml with distilled water, and the pH was adjusted to 5.6. The solution was sealed and sterilized as described above.

The medium was dissolved by heating prior to use and 5 ml of glucose stock solution and 250 µl of AS stock solution were added, and the aliquots were poured into petri dishes (25 ml/dish).

6) Screening Medium:

| | |
|---|---|
| $N6_{max}$ stock solution (10X) | 25 ml |
| $N6_{mix}$ stock solution (100X) | 2.5 ml |
| $Fe^{2+}$EDTA stock solution (100X) | 2.5 ml |

-continued

| | | |
|---|---|---|
| Vitamin storage solution (100X) | 2.5 | ml |
| 2,4-D stock solution | 0.625 | ml |
| CH | 0.15 | g |
| Sucrose | 7.5 | g |
| Agar powder | 1.75 | g |

They were added to 250 ml with distilled water, and the pH was adjusted to 6.0. The solution was sealed and sterilized as described above.

The culture medium was dissolved prior to use, and 250 μL of HN (50 mg/ml) and 400 μL of CN (10 g CN/36 ml of water) were added. The medium was poured into petri dishes (25 ml/dish). (Note: Concentration of carbenicillin in the first screening medium was 400 mg/L and that in the second and later screening medium was 250 mg/L).

7) Pre-Differentiation Medium (Japonica Rice without this Step):

| | | |
|---|---|---|
| $N6_{max}$ stock solution (10X) | 25 | ml |
| $N6_{mix}$ stock solution (100X) | 2.5 | ml |
| $Fe^{2+}$EDTA stock solution (100X) | 2.5 | ml |
| Vitamin storage solution (100X) | 2.5 | ml |
| 6-BA stock solution | 0.5 | ml |
| KT stock solution | 0.5 | ml |
| NAA stock solution | 50 | μL |
| IAA stock solution | 50 | μL |
| CH | 0.15 | g |
| Sucrose | 7.5 | g |
| Agar powder | 1.75 | g |

They were added to 250 ml with distilled water, and the pH was adjusted to 5.9 with IN potassium hydroxide. The solution was sealed and sterilized as described above.

The culture medium was dissolved prior to use, 250 μl of HN (50 mg/ml) and 250 μl of CN (250 mg/ml) were added. The medium was poured into petri dishes (25 ml/dish).

8) Differentiation Medium:

| | | |
|---|---|---|
| $N6_{max}$ stock solution (10X) | 100 | ml |
| $N6_{mix}$ stock solution (100X) | 10 | ml |
| $Fe^{2+}$EDTA stock solution (100X) | 10 | ml |
| Vitamin storage solution (100X) | 10 | ml |
| 6-BA stock solution | 2 | ml |
| KT stock solution | 2 | ml |
| NAA stock solution | 0.2 | ml |
| IAA stock solution | 0.2 | ml |
| CH | 1 | g |
| Sucrose | 30 | g |
| Phytagel | 3 | g |

They were added to 900 ml with distilled water, and the pH was adjusted to 6.0 with IN potassium hydroxide.

The medium was boiled and made up to 1000 ml with distilled water. They were aliquoted into a 100 ml triangular flask (50 ml/flask), sealed, and sterilized as described above.

9) Rooting Medium

| | | |
|---|---|---|
| $MS_{max}$ stock solution (10X) | 50 | ml |
| $MS_{mix}$ stock solution (100X) | 5 | ml |
| $Fe^{2+}$EDTA stock solution (100X) | 5 | ml |
| Vitamin storage solution (100X) | 5 | ml |
| Sucrose | 20 | g |
| Phytagel | 3 | g |

They were added to 900 ml with distilled water, and the pH was adjusted to 5.8 with IN potassium hydroxide.

The medium was boiled and made up to 1000 ml with distilled water. They were aliquoted into a rooting tube (50 ml/tube), sealed, and sterilized as described above.

(4) Steps for *Agrobacterium*-Mediated Genetic Transformation:

4.1 Callus Induction

1) The mature Zhonghua 11 rice seeds were hulled and then treated with 70% ethanol for 1 minute, followed by disinfection of the seed surface with 0.15% mercury chloride (HgCl2) for 15 minutes;
2) The seeds were washed 4-5 times with sterilized water;
3) Placing 8-10 seeds on the induction medium;
4) The inoculated medium was incubated in the dark for 4-5 weeks at a temperature of 26±1° C.

4.2 Callus Subculture:

Bright yellow, compact and relatively dry embryogenic calli were selected and cultured on the subculture medium for 2 weeks in the dark at a temperature of 25±1° C.

4.3 Pre-Culture:

The compact and relatively dry embryogenic calli were selected and cultured in the dark on a pre-culture medium for 2 weeks at a temperature of 26±1° C.

4.4 *Agrobacterium* Culture:

1) The LA medium with corresponding resistance (J. Sambrook et al., Molecular Cloning Experiment Guide, Third Edition, Jin Dongyan et al. (translation), Science Press, 2002, Beijing is referred for preparation of the LA medium) was used for streak culture of the *Agrobacterium* EHA105 (an *Agrobacterium* strain publicly used by CAMBIA) at a temperature of 28° C. for two days;
2) The *Agrobacterium* was transferred to a suspension medium and incubated on a 28° C. shaker for 2-3 hours.

4.5 *Agrobacterium* Infection:

1) The pre-cultured calli were transferred into a sterile bottle;
2) The suspension of *Agrobacterium* was adjusted to a OD600 of 0.8-1.0;
3) The calli were immersed into the suspension of *Agrobacterium* for 30 minutes;
4) The calli were transferred to a sterilized filter paper for suction drying; and then placed on a co-culture medium for 3 days at a temperature of 19-20° C.

4.6 Washing and Selective Culture for Calli:

1) The calli were washed with sterilized water until the *Agrobacterium* was not visible;
2) The calli were immersed into a sterilized water containing 400 mg/L carbenicillin (CN) for 30 minutes;
3) The calli were transferred to a sterilized filter paper for suction drying;
4) The calli were transferred to the screening medium for selective culture 2-3 times for 2 weeks each time until resistant calli grew out.

4.7 Differentiation:

1) The resistant calli were transferred to pre-differentiation medium for 5-7 days in the dark;
2) The calli subjected to the pre-differentiation culture were transferred to the differentiation medium, and cultured under light for 5 to 6 weeks at a temperature of 26° C. until large seedlings grew out. Three independent calli were evenly distributed in each flask.

4.8 Rooting and Hardening-Seedling:

1) The old roots produced at differentiation were cut off;
2) After transferring them to the rooting medium for 2-3 weeks under light until large seedlings grew out, the sealing film was removed and a part of the tap water was added to the seedlings for one week to be transplanted at a temperature of 26° C.

4.9 Transplant

The residual medium on the roots was washed off, and the seedlings with good roots were transferred to a greenhouse while keeping moist for the first few days. The seedlings were transplanted to the field when they grew well.

A total of 14 TO generation of rice plants with independent transgenic complementarity including 7 positive individual plants and 7 negative individual plants were obtained in this experiment. The positive plants were planted in a field, and the pollens were taken when rice head sprouting and flowering occurred, and then subjected to potassium iodide staining and microscopic inspection. The fertile pollen rate of TO generation of plants reached more than 80%, and the seed setting rate of self-crossing spikelets reached more than 60%. However, the fertile pollen rate of the control sterility line was zero, and the self-crossing spikelets was not seed setting. The seeds of the TO generation of plants were harvested and planted in the field to observe the phenotype of the Tl generation. Phenotypic investigation was carried out at the maturity stage, and as shown in FIGS. 3A-3E, the segregation of fertility and sterility occurred in the population of Tl generation, and the seed setting rate of fertile individual plants was above 70%, while the seed setting rate of sterile individual plants was zero. The results of this experiment indicated that a new restorer line can be created by transforming the restorer gene OsRf19 into a sterile variety which does not contain functional OsRf19. This experiment also demonstrated that the biological function of the gene is to restore the fertility for cytoplasmic male sterility. The gene from the OsRf19 locus obtained from the genome of the restorer line of rice was identified as the gene of interest, i.e., the restorer gene OsRf19 for cytoplasmic male sterility.

The $F_1$ generation of plants were obtained by crossing the Tl generation of positive plants transduced with the OsRf19 gene with the new cytoplasm derived sterility line Xinzhi 1A (see Chinese rice varieties and their pedigree database website: https://www.ricedata.cn/variety/varis/621300.htm). $F_1$ generation of plants and the sterility line Xinzhi 1A were planted in a field in Wuhan, and the pollens were taken when rice head sprouting and flowering occurred, and then subjected to potassium iodide staining and microscopic inspection. As shown in FIGS. 4A-4B, the pollens of Xinzhi 1A were sterile after being stained with potassium iodide, and the seed setting rate was zero; The pollens of $F_1$ generation of plants were fertile after being stained with potassium iodide, and the seed setting rate was more than 80%. This experiment also demonstrated that the restorer line created after transduction with the restorer gene OsRf19 is able to restore the fertility of the new cytoplasm derived sterility line.

Example 6: Expression Analysis of OsRf19

The expression of this gene was analyzed by RT-PCR. The primer sequences used for RT-PCR are shown below in SEQ ID NO: 7 and SEQ ID NO: 8.

```
SEQ ID NO: 7:
5'-GATGTACTTTGCAAGTCAGG-3';

SEQ ID NO: 8:
5'-CCTTCTTTGCAAAGATTGCT-3';
```

Figure 5:
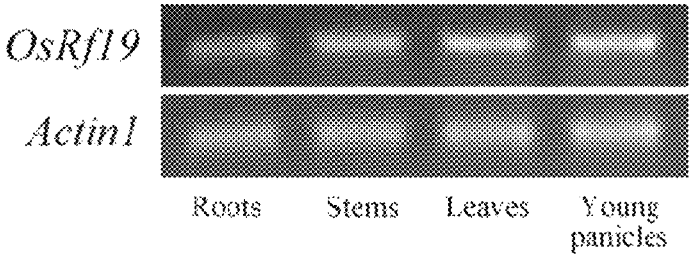
FIG. 5 is a RT-PCR diagram for detection of expression characteristics of the gene OsRf19 of the present application. The upper is the expression of the gene of interest OsRf19 in each tissue; and the lower is the expression of the internal reference gene Actin1 in each tissue.

RT-PCR analysis results are shown in FIG. 5. The results in FIG. 5 show that the OsRf19 gene in Jinhui 3 is expressed in various tissues, such as roots, stems, leaves and young panicles, i.e., constitutively expressed, and therefore belongs to a constitutively expressed gene.

Example 7: Restoration of the Fertility of a Sterility Line by a Restorer Line Containing the Restorer Gene OsRf19

In this example, restorer lines of rice Jinhui 3 (which is a parent of an approved variety Jinnong 3 You 3 and is available from China National Seed Group Corporation, Ltd.) and Huazhan-RFFA (both containing the restorer gene OsRf19) were combined with the sterility lines of rice Jinnong 3A (which is a parent of an approved variety Jinnong 3 You 3 and is available from China National Seed Group Corporation, Ltd.) and the Xinzhi 1A (variety right number: CNA20162267.2) (both containing the sterility gene orf182) to demonstrate the restoration of the fertility of the sterility line containing the sterility gene orf182 by the restorer gene OsRf19.

The restorer line Huazhan-RFFA used in this example was obtained by crossing Jinhui 3 as the donor parent with Huazhan as the acceptor parent, and introducing the restorer gene OsRf19 into the acceptor parent after 4 backcrosses.

The seeds of the restorer line Huazhan-RFFA were deposited on China Center for Type Culture Collection at Wuhan University, Wuhan, China with the following information on Jun. 20, 2022:

Deposition institution: China Center for Type Culture Collection (CCTCC)

Address: Wuhan University, Wuhan, Hubei, China

Date of deposit: Jun. 20, 2022

Culture Name (Taxonomic Nomenclature): *Oryza sativa* Seed Huazhan-RFFA

Accession number: CCTCC NO: P202217.

A deposit of Huazhong Agricultural University and China National Seed Group Corporation, Ltd. proprietary seeds of the restorer line disclosed above and recited in the appended claims has been made with the China Center for Type Culture Collection (CCTCC) (Wuhan University, Wuhan, China) and has been accepted under the terms of the Budapest Treaty. The date of deposit was Jun. 20, 2022. The deposit of 2,000 seeds was taken from the same deposit maintained by the Huazhong Agricultural University (No. 1, Shizishan Street, Hongshan District, Wuhan, Hubei 430070, China) and China National Seed Group Corporation, Ltd. (17/F You'an International Building, Xitieying Middle Road, Fengtai District, Beijing 100069, China) since prior to the filing date of this application. The CCTCC Accession Number is P202217. The deposit will be maintained in the depository for a period of thirty years, or five years after the last request, or for the enforceable life of the patent, whichever is longer, and will be replaced as necessary during that period. All restrictions upon availability of the biological material to the public will be irrevocably removed upon granting of the patent for the enforceable life of the patent in accordance with 37 CFR § 1.808(a)(2), and the deposit is intended to meet all of the requirements of 37 CFR. §§ 1.801-1.809.

In order to demonstrate the restoration ability of the restorer lines, we used the new cytoplasm derived restorer lines Huazhan-RFFA and Jinhui 3 to hybridize with the new cytoplasm derived sterility lines Jinnong 3A and Xinzhi 1A, respectively. The seed setting rates of $F_1$ hybrids were investigated. The results showed that the seed setting rates of $F_1$ generations of crossing of the restorer lines Huazhan-RFFA and Jinhui 3 with Jinnong 3A and Xinzhi 1A were 79.6%-85.8% (Table 1).

TABLE 1

| Female parent | Male parent | Setting rate |
|---|---|---|
| Jinnong 3A | Huazhan -RFFA | 80.7% |
| Jinnong 3A | Jinhui 3 | 79.6% |
| Xinzhi 1A | Huazhan -RFFA | 85.8% |
| Xinzhi 1A | Jinhui 3 | 82.5% |

In addition, in this example, $F_1$ hybrids were obtained by crossing the existing Yebai restorer lines Minghui 63 and Gui 99 as a male parent with Jinnong 3A and Xinxin 1A, respectively. Four combinations of hybrids were then planted in the field to investigate the seed setting rates, and the results showed that the seed setting rates of the hybrids of Minghui 63 and Gui 99 with Jinnong 3A and Xinzhi 1A were 0, respectively. Through the experiment, it is proved that the Yebai restorer line has no restoring ability to the new cytoplasm derived sterility line.

The invention claimed is:

1. An expression vector, comprising a restorer gene OsRf19 for cytoplasmic male sterility in rice, wherein the restorer gene OsRf19 comprises the nucleotide sequence set forth in SEQ ID NO: 1, and at least one heterologous expression control sequence operably linked to the restorer gene OsRf19.

2. A method of creating a restorer line of rice, comprising introducing into a rice variety the expression vector of claim 1.

3. The method according to claim 2, wherein the rice variety is selected from the group consisting of upland rice, indica rice, japonica rice, early rice, late rice, viscous rice, glutinous rice, rice with hairy leaves, and rice without hairy leaves.

4. A method of restoring the fertility of a cytoplasmic male sterility line of rice, comprising:

introducing into a rice variety the expression vector of claim 1 to produce a transgenic restorer line; and crossing the transgenic restorer line with the cytoplasmic male sterility line to produce hybrid seeds having normal fertility.

5. The method according to claim 4, wherein the rice variety, the cytoplasmic male sterility line of rice and the restorer line of rice is independently selected from the group consisting of upland rice, indica rice, japonica rice, early rice, late rice, viscous rice, glutinous rice, rice with hairy leaves, and rice without hairy leaves.

6. The method according to claim 4, wherein the cytoplasmic male sterility line of rice is a new cytoplasm derived sterility line, and the new cytoplasm derived sterility line is a sterility line of rice containing a sterility gene, wherein the sterility gene is the chimeric mitochondrial gene (orf182).

7. The method according to claim 6, wherein the sterility gene orf182 comprises the nucleotide sequence set forth in SEQ ID NO: 9.

8. A restorer line of rice or the seeds thereof, which is created by the method according to claim 2, wherein the line of rice and the seeds comprise the expression vector.

9. A cytoplasmic male sterility line of rice or the seeds thereof, wherein the seeds have the Accession number of China Center for Type Culture Collection (CCTCC) NO: P202115.

10. A combination of rice varieties, which comprises the restorer line of rice or the seeds thereof of claim 8, a cytoplasmic male sterility line of rice or the seeds thereof and a maintainer line of rice or the seeds thereof.

11. The combination of claim 10, wherein the seeds of the cytoplasmic male sterility line of rice has the Accession number of CCTCC NO: P202115.

12. The expression vector of claim 1, wherein the restorer gene OsRf19 further comprises the nucleotide sequences set forth in SEQ ID NOs: 2 and 3.

13. The method according to claim 2, wherein the introducing is carried out by gene editing, and wherein the gene editing is carried out by one or more selected from the group consisting of CRISPR/Cas9, CRISPR/Cas12a, TALEN, meganuclease, ZFN, DddA derived cytosine base editors, and TALED.

14. The method according to claim 4, wherein the introducing is carried out by gene editing, and wherein the gene editing is carried out by one or more selected from the group consisting of CRISPR/Cas9, CRISPR/Cas12a, TALEN, meganuclease, ZFN, DddA derived cytosine base editors, and TALED.

15. The restorer line of rice or the seeds thereof of claim 8, wherein the seeds have the Accession number of CCTCC NO: P202217.

16. A method of producing rice hybrid seeds, comprising: crossing a cytoplasmic male sterility line of rice as a female parent and the restorer line of rice of claim 8 as a male parent to produce rice hybrid seeds.

17. The method according to claim 16, wherein the rice variety, the cytoplasmic male sterility line of rice and the restorer line of rice is independently selected from the group consisting of upland rice, indica rice, japonica rice, early rice, late rice, viscous rice, glutinous rice, rice with hairy leaves, and rice without hairy leaves.

18. The method according to claim 16, wherein the cytoplasmic male sterility line of rice is a new cytoplasm derived sterility line, and the new cytoplasm derived sterility line is a sterility line of rice containing a sterility gene, wherein the sterility gene is the chimeric mitochondrial gene (orf182).

19. The method according to claim 18, wherein the sterility gene orf182 comprises the nucleotide sequence set forth in SEQ ID NO: 9.

* * * * *